(12) United States Patent
Fuhr et al.

(10) Patent No.: US 6,931,864 B2
(45) Date of Patent: Aug. 23, 2005

(54) CRYOSTORAGE METHOD AND DEVICE

(75) Inventors: Günter Fuhr, Berlin (DE); Rolf Hagedorn, Berlin (DE); Heiko Zimmermann, St. Ingbert (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 23 days.

(21) Appl. No.: 10/433,691

(22) PCT Filed: Dec. 7, 2001

(86) PCT No.: PCT/EP01/14400

§ 371 (c)(1),
(2), (4) Date: Sep. 8, 2003

(87) PCT Pub. No.: WO02/46719

PCT Pub. Date: Jun. 13, 2002

(65) Prior Publication Data

US 2004/0065093 A1 Apr. 8, 2004

(30) Foreign Application Priority Data

Dec. 7, 2000 (DE) .......................................... 100 60 889
Sep. 12, 2001 (DE) .......................................... 101 44 925

(51) Int. Cl.[7] .......................... F25D 25/00; C12M 1/00; C12M 3/00; G06F 17/00
(52) U.S. Cl. .......................... 62/62; 435/307.1; 707/100
(58) Field of Search .............................. 62/62; 435/1.3, 435/284.1, 307.1, 260; 707/100

(56) References Cited

U.S. PATENT DOCUMENTS

| | | | |
|---|---|---|---|
| 3,551,023 A | * | 12/1970 | Brackett ........................ 156/60 |
| 4,969,336 A | | 11/1990 | Knippscheer et al. |
| 5,233,844 A | * | 8/1993 | Knippscheer et al. ......... 62/440 |
| 5,252,294 A | * | 10/1993 | Kroy et al. .................. 422/102 |
| 5,275,016 A | | 1/1994 | Chatterjee et al. |
| 5,561,556 A | * | 10/1996 | Weissman .................... 359/396 |
| 5,759,846 A | * | 6/1998 | Stoppini et al. ......... 435/284.1 |
| 5,840,256 A | * | 11/1998 | Demers et al. .............. 422/102 |
| 5,921,102 A | | 7/1999 | Vago |
| 5,925,511 A | | 7/1999 | Fuhr et al. |
| 6,215,894 B1 | * | 4/2001 | Zeleny et al. ................ 382/133 |
| 6,362,004 B1 | * | 3/2002 | Noblett .......................... 436/43 |
| 6,646,238 B1 | | 11/2003 | Fuhr et al. |
| 2002/0108957 A1 | | 8/2002 | Studer |

FOREIGN PATENT DOCUMENTS

| | | |
|---|---|---|
| DE | 196 21 179 A1 | 11/1997 |
| DE | 197 52 085 A1 | 6/1998 |
| DE | 197 16 913 A1 | 11/1998 |
| DE | 197 25 768 A1 | 12/1998 |
| DE | 197 36 470 A1 | 3/1999 |
| DE | 198 26 350 A1 | 12/1999 |
| DE | 198 38 232 A1 | 3/2000 |
| DE | 198 41 554 A1 | 3/2000 |
| DE | 199 05 163 A1 | 8/2000 |
| DE | 199 21 236 A1 | 11/2000 |
| DE | 199 22 310 A1 | 11/2000 |
| EP | 0 347 579 A2 | 12/1989 |
| EP | 0 475 409 A2 | 3/1992 |
| EP | 0 706 825 A1 | 4/1996 |
| EP | 0 804 073 B1 | 11/1997 |
| EP | 0 853 238 A1 | 7/1998 |

\* cited by examiner

*Primary Examiner*—William C. Doerrler
(74) *Attorney, Agent, or Firm*—Caesar, Rivise, Bernstein, Cohen & Pokotilow, Ltd.

(57) ABSTRACT

With a method for cryo-preservation, at least one specimen is arranged on a storage substrate and specimen data, which are characteristic for features of the specimen, are stored at specific positions. Also, a storage substrate for cryo-preservation with such a method is described.

21 Claims, 17 Drawing Sheets

123

CRYOSTORAGE METHOD AND DEVICE

BACKGROUND OF THE INVENTION

The present invention relates to methods for cryo-storage of specimens, in particular, for the production, storage, and manipulation of biological specimens in a cryo-preserved or in a thawed condition, such as, for example, a cryo-preservation method for biological cells. The invention relates also to methods for writing and reading of data. The invention further relates to a device for cryo-storage of specimens, in particular, a storage substrate for biological specimens, such as, for example, cells or cell components, a device for writing and reading of data in storage media and a cryo-bank system. The invention also relates to uses of the cryo-preservation of biological specimens.

Cryo-preservation is a commonly known method for maintaining in particular biologically or medically relevant materials. These materials include, for example, tissue and organs, body fluids, or also individual cells or cell components. The cryo-preservation takes place according to pre-determined procedures in containers or on substrates, whose shape is adapted to the material or specimen. Containers for cryo-preservation are known, for example, for tissue and organs (see DE-OS 199 22 31, EP-A 0 853 238, DE-OS 197 25 768, DE-OS 199 05 163), for blood components (see, for example, DE-OS 198 26 350), and for cell or drop-shaped cryo-specimens (see, for example, U.S. Pat. No. 5,275,016, EP-B 0 475 409, DE-OS 199 21 236, EP-B 0 804 073).

A general concern with the cryo-preservation of biological specimens is in the ability of the specimen to be identified. Cryo-preservation specimens must be able to be identified with reference to their origin and characteristics with a high degree of certainty, without the necessity of thawing. With the macroscopic specimens, this is not a problem, since organ or blood containers can be provided with an inscription. Locating the cryo-specimen takes place in dependence on storage systems of the respective cryo-bank.

With small cryo-specimens in the form of frozen suspension drops, cells, cell aggregates, or cell components, the identification of the cryo-specimens is considerably problematic. A cryo-specimen would be negligibly small compared with the inscription. Often, an interest exists in the cryo-preservation of a plurality of microscopically small specimens. The storing and identification of small cryo-specimens with inscriptions would be impractical. In addition, the cryo-preserved cell specimens are available in a disordered state with common preservation techniques, which are based on the spraying of cell suspensions on cool surfaces (see, for example, EP-B 0 475 409). Only large amounts of individual specimens can be preserved commonly and unspecifically.

With the preservation techniques described in EP-B-8-4 073 and DE-OS 199 21 236, an arranged placement and specific processing of even the smallest specimens on the cryo-substrates is possible. The specimen deposition takes place, for example, with the use of a micro-drop shooting device, which is controlled on the basis of predetermined target coordinates. The specimens are located on defined substrate positions, on which also a specific measurement of specimen properties and identification of the specimens is possible. The substrate can be provided with a marking, in order to define the specimen positions on the substrate. For example, in DE-OS 199 21 236, for the matrix-type deposition of cryo-specimens in straight lines and columns, it is proposed that the substrate is provide with a designation of the columns and lines. This marking technique is illustrated in FIG. 27 (prior art).

The conventional marking of cry-substrates according to FIG. 27 has the following disadvantages. While the identification of specimens is possible, however, only information about the positions is provided. The limited information content of the substrate marking, however, represents a problem since, in addition to the specimen identification, also additional data, for example, about the condition or the history of the specimen or about measurement results should be available. These data can be stored in a parallel-operated data bank. The separate operation of cryo- and data banks, however, represents a considerable risk for the certainty of the feature allocation to the individual specimens. This risk is critical in particular with human medical uses, since a specific mistake can defeat the success of a further use of the cryo-specimen. In addition, the substrate marking has the disadvantage that specimen identification is possible only in connection with the cryo-substrate. When a specimen removal takes place, for example, such as that described in DE-OS 199 21 236, after separation from the cryo-substrate, a specimen identification can take place only by an expensive measurement of specific characteristics in a thawed state.

From DE-OS 197 52 085, a specimen carrier for microscopic analysis of a plurality of specimens is known. The conventional specimen carrier is formed as a substrate with a plurality of specimen receiving spaces, as shown in FIG. 28 in schematic plan view (prior art). The substrate, for example, has the shape of a plate storage medium (for example, a CD). Between a passage hole in the substrate center and the associated matrix-type specimen-receiving spaces, a ring region is formed. From DE-OS 197 52 085, it is known to form these ring regions for storing specimen data. The common specimen carrier has the disadvantage that it can only be used for receiving liquid specimens and not for cryo-preservation. In addition, the storage of specimen data on the inner ring represents the same disadvantage as the above-described substrate marking. More data can be stored; however, the association to the individual specimens is not possible without errors.

In addition to the noted disadvantages of the common technology, the following basis also exists for the minimally developed use, until now, of cryo-preservation, in particular, in cellular biotechnology. If a direct freezing of biological specimens takes place in a liquid cooling phase (for example, nitrogen), a risk of contamination exists. Over the cooling phase, viruses can be transmitted to the specimens. In order to avoid this risk, the contact with the liquid phase must be avoided or a sealed covering of the specimens must take place. Up to now, this has not been able to be realized in a practical manner.

From labor technology, specimen carriers, for example, in the form of object carriers or micro-titer plates are known, which are equipped with data storage media. These conventional specimen carriers are not suited for cryo-storage. First, they are merely suited for a use at ambient room temperature or a refrigerator temperature above the freezing point of water. A use at low temperatures has not been provided up to this point. Second, conventional specimen carriers are provided as substrates for specimens. Treatment, manipulation, or cultivation of the specimens takes place on the substrates. For storage in a preserved state, the conventional specimen carriers, however, are not suitable. In this connection, the containers for cryo-preservation are used, as described above. Finally, the conventional specimen carriers are not suitable for an effective specimen storage and manipulation. In practice, they must be manually transported; storage with high density is impossible.

The object of the present invention is to provide an improved method for cryo-preservation, with which the disadvantages of the conventional techniques are overcome, which has a broader range of use, and in particular, which is suited for automated preservation storage. The new method for cryo-preservation should make possible, in particular, that the specimen data are accommodated in greater amounts and with a higher data certainty (that is, with increased certainty of the association of specimen data to determined specimens). The invention also makes possible a highly specific data association to individual cryo-specimens. The object of the invention is also to provide devices for implementation of the improved cryo-preservation methods described above.

BRIEF SUMMARY OF THE INVENTION

The basic idea of the present invention is to arrange at least one specimen on a substrate and on the substrate, to provide storage of specimen data, which are characteristic for the features of the cryo-specimen. The storage of the specimen data takes place position-specific in a specimen data storage medium, preferably, at the storage position of the respective specimen. By means of the storage of specimens and specimen data on common or closely adjacent or adjoining positions of the substrate, a series of advantages is achieved. The specimen data are clearly associated by means of their storage positions to the respective specimens. A mistake in specimen association is impossible. Upon removal of specimens, the associated data can be simultaneously read or removed with the storage medium from the substrate, so that also, after the removal of the specimen, with further processing, the identification of the specimen and the association of the specimen data are ensured. A removal of individual specimens at desired temperatures, in particular, also in a frozen state, can take place.

A considerable improvement that can be achieved with the present invention is that, first, methods and suitable devices can be provided, which are directly optimal for storage and preservation of biological specimens over long periods of time (months and years) at low temperatures (for example, below −50° C.). With the invention, a new area of use with operating temperatures for the use of data storage has been made available, which, prior to the invention, was not utilized.

Depending on the use, the specimen deposition and the data storage can take place at ambient room temperature with subsequent cooling to a required preservation temperature or also in a cooled state. The inventors have surprisingly found that writing as well as reading of data in or out of the known storage media (for example, optical storage, magnetic storage, electromagnetic storage, FLASH storage), or in special storage media for the object of cryo-storage at preservation temperatures beneath the freezing point of water are possible. The specimen data sets are reliably readable in all phases of a cryo-preservation process. The readability of data storage at these types of low temperatures, that likewise, exclude a writing of data, represents an advantage known to the inventors, which amounts to a broader usability of the inventive cryo-storage.

Particularly advantageous to the present invention is the deposition of a plurality of specimens on a common storage substrate with a position-specific storage of a plurality of specimen data sets. The storage substrate serves simultaneously as a cryo-substrate with specimen carriers for receiving, retaining, and releasing cryo-specimens and as data carriers, which stores a plurality of data on the substrate position corresponding to the respective specimen positions, as in a storage medium known in computer technology. The specimens are applied in portions (for example, in drops) and isolated from one another as cell suspension volumes (for example, as cell suspension drops) on or in the specimen carrier of the cryo-substrate. Each specimen carrier is associated with a specimen data storage medium, in which associated data are stored. The simultaneous storage of specimens and specimen data takes place, such that it is stable over long periods of time and it is safeguarded from mix-ups. The inventive cryo-preservation is designated as "cryo-storage", because of the analogy to electronic data storage.

According to a preferred embodiment of the invention, the cryo-storage takes place on a storage substrate with at least one cryo-storage element. Each cryo-storage element includes a specimen carrier and a specimen data storage, which form therewith an integral component, which is removable reversibly or irreversibly from the substrate. The specimen carrier and the data storage form a secure connection, which is attached removably on the storage substrate for cryo-storage. In order to remove a specimen from the storage substrate, the entire cryo-storage element is removed from the storage substrate. A subject of the present invention is also the cryo-storage element, which includes a specimen carrier for receiving a cryo-specimen and a specimen data storage for storage of associated specimen data. According to a preferred embodiment of the invention, a storage substrate is formed by a base body, which preferably has a flat shape, with a plurality of cryo-storage elements. The storage substrate can have a predetermined two- or three-dimensional geometric form, depending on the use. According to a preferred embodiment of the invention, the base body of the storage substrate has the form of an optical storage plate (CD-ROM), in which the cryo-storage elements are integrated, or at least one circuit board, on which the cryo-storage elements, like electrical circuits (chips), are placed.

A subject of the present invention is also a method for operating a cryo-bank with a plurality of storage substrates. On at least one storage substrate, a plurality of specimens are stored, which, for example, belong to an organism (test subject). The specimens include, for example, one or more specific cells of the test subject (for example, stem cells, tissue cells). First, the storage of the specimens takes place commonly with the specimen-specific data, in particular, data for identification of the type of specimen and test subject, identification of the preservation time point, and identification of measurement data at the time point of the preservation. In the operation of the cryo-bank, specimens are removed commonly with the associated specimen data for measurement purposes, diagnostic objectives, or therapeutic methods, and/or to supplement further specimens or specimen data. The specimen data include generally all features and parameters of the specimen and the specimen donor, and if need be, additional information for data storage on the storage substrate. An inventively used specimen data storage has a storage capacity of at least 4 megabytes, for example.

By means of the following advantageous features of the inventive cryo-storage, the disadvantages of conventional planar or three-dimensional substrates are overcome. The specimens (for example, frozen cell suspension volumes) are specifically accessible at any point in time. This is also true for a low temperature state. The smallest specimen volumes can be arranged at defined substrate positions, which have characteristic dimensions in the mm-range or less, preferably, however, typically amounts of $10^3$ $\mu m^3$ ($10 \cdot 10 \cdot 10 \mu m^3$) to some 10 $nm^3$. The specimens can contain, for example, one or a plurality of cells ($10^5$ to $10^6$ cells), cell components, biologically relevant objects (such as, for example, membrane vesicles, DNA materials, macromolecules) and/or cell bonds. The specimens can be arranged with a high density, the cryo-storage having an increased effectiveness.

The specimens can be removed selectively in a deep-cooled state of the storage substrate, without interrupting the cooling of the remaining specimens. For specimen reduction and data reading, no thawing of the entire storage substrate is necessary.

The specimen data can be automatically written or read supported by a computer. The association of the specimen data storage and specimen carriers is unique. The specimens are stored, such that they are safeguarded from misidentification. The association of the removed specimens to the specimen data and also to the storage substrate is maintained, so that the history of a specimen can be recapitulated. This represents a particular advantage with medical uses of the invention.

The cryo-storage elements of the present invention are preferably made with the use of low-temperature compatible plastic material, which, on the one hand, forms the specimen carrier and on the other hand, forms an embedding for the specimen data storage. The plastic material can tolerate repetitious temperature changes without change and without damage. Preferably, a plastic material is used, whose water absorption capacity amounts to <1% of the dead weight, in particular, <0.1% of the dead weight. The cryo-storage elements according to the present invention are based, for example, on polyurethane, poly-tetra-fluoroethylene, or polyethylene. The storage substrate of the present invention advantageously has a high mechanical stability and a long-term durability. The inventive cryo-storage makes possible for the first time a secure storage of biological specimens over decades. A cryo-bank can be reliably operated over the entire longevity of a donor (test subject), for example, for the duration of a human life. The storage substrate has a relatively simple structure, which makes possible an abundant use of the storage substrates in cryo-banks.

The invention also has advantages with reference to the noted contamination risks. The inventive storage substrate makes possible a series of features to be described below, by means of which a liquid cooling medium is prevented from coming into contact with the specimens. Viral contamination is avoided over the cooling phase. Also, the condensation of water or other substances on the specimens is impossible.

A further important advantage of the storage substrate of the present invention is that the stored specimens are accessible in a cryo-preserved or thawed state of the common measurement and analysis methods (for example, optical measurement, microscopic analyses) with simultaneous readability of the data phases. The data in the specimen data storages are also maintained with multiple freezing or thawing processes.

The cryo-storage takes place with conservation conditions chosen depending on the application. The temperature of the cryo-storage and the chronological cycle of decreases or increases in temperature are selected based on the preservation object and the material. The preservation temperature lies in a region below the ambient room temperature, preferably, below the freezing point of water with normal pressure and with the preferred long-term use, below $-80°$ C. The cryo-temperature is preferably adjusted by means of a liquid cooling medium (nitrogen) or the vapor of the cooling medium.

The invention has the advantage that the smallest specimen volumes can be cryo-preserved. This makes possible fast temperature changes, reproducible preservation conditions, and an individual specimen manipulation, treatment, or measurement.

BRIEF DESCRIPTION OF SEVERAL VIEWS OF THE DRAWINGS

Further advantages and characteristics of the invention are described with reference to the attached drawings. In the drawings.

DETAILED DESCRIPTION OF PREFERRED EMBODIMENTS OF THE INVENTION

According to the present invention, at least one specimen is arranged in a specimen carrier on a substrate and on the substrate, storage of specimen data is made, which are characteristic for features of the cryo-specimen. The storage of the specimen data takes place position-specific in a specimen data storage, preferably, at the storage position of the respective specimen. The connection on a specimen carrier for receiving a cryo-specimen and a specimen data storage for storage of associated storage data is designated as a "cryo-storage element". An inventive storage substrate is preferably formed as a base body, which preferably, has a flat form, with a plurality of cryo-storage elements.

Figure 1:
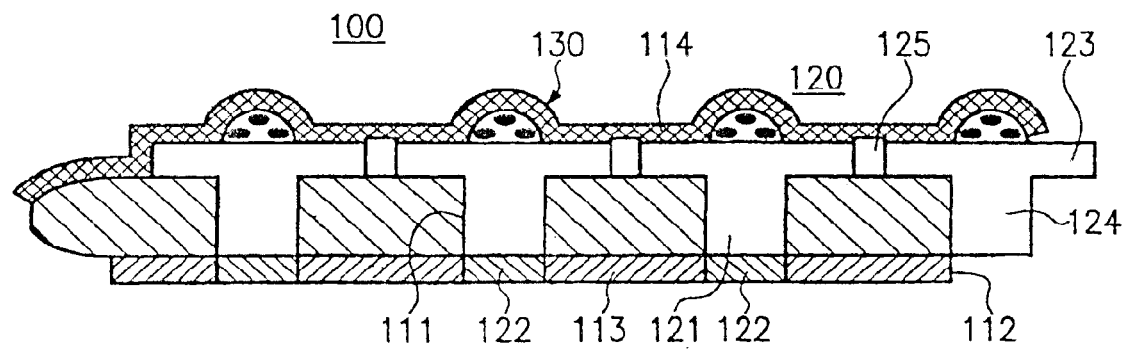
FIG. 1 is a schematic sectional view of a part of the inventive storage substrate according to a first embodiment of the invention.

With the first embodiment of the inventive storage substrate 100 shown in FIG. 1, a base body 110 is provided, which supports a plurality of cryo-storage elements 120. The base body 110 (shown in cut-away manner) has typical dimensions, such as, for example, an optically readable/writable storage plate (in the following: CD, diameter approximately 12 cm, for example). For receiving the cryo-storage element 120, the base body 110 has passage openings 111, in which the cryo-storage elements sit in a type of a press fit. On one side of the base body 110, a film-type storage medium 112 is arranged. The storage medium 112 is a data layer, such as the type that is known for common CD's and that is suitable for reading and writing of data. The storage medium 112 preferably is designed for optical writing ("burning") and reading of data. However, it also can be a magnetic or a topographic storage medium. On the storage medium 112, a protective layer is provided, if necessary (not shown).

The storage medium 112 includes layer regions, which lie on the base body 110 and serve as base storage 113, and regions, which are associated with the cryo-storage elements 120 and serve as specimen data storage 122. The base storage 113 and specimen data storage 122 first can form a closed layer of the storage medium 112, which after specimen removal (see FIG. 2) is broken, when necessary. The base storage 113 contains preferably substrate data, which, for example, relate to the type of the arrangement of the cryo-storage elements and the identification of the substrates. The specimen data storage 122 contains specimen data (see below).

The cryo-storage elements 120 comprise, respectively, a specimen carrier 121 and the specimen data storage 122. The specimen carrier 121 is a formed component made of plastic with a T-shape, plate-shape, or mushroom shape. The specimen carrier, instead of being made of plastic, can comprise a bio-compatible and inert material (for example, semiconductor material). The specimen carrier 121 includes a plate-type specimen receptacle 123 and a carrier pin 124. The inner shape of the passage openings 111 and the outer shape of the carrier pin 124 are complementary for forming a press-fit to one another. Between the edges of the specimen receptacles 123, gaps 125 are formed. The gaps 125 reduce the risk of a mutual contamination between the specimens. In addition, they simplify the removable from the cryo-storage elements. With the carrier pins 124, the respective specimen storage 122 is securely connected.

On the specimen receptacles 123, the cryo-specimens 130 are arranged, in particular, in the form of frozen liquid drops. The drops are cell suspensions or also reference specimens, for example, with samples of cultivation media, solutions of marking dyes, or probe specimens. Probe specimens are reference specimens, which contain substances that react sensitively to a change of critical environmental conditions. As probe samples, for example, chemical compounds can be used, which are sensitive to radioactive radiation or unwanted temperature increases. A control of the probe specimen makes possible a monitoring of the storage condition of the storage substrate in a cryo-bank.

A cover film 114 is arranged over the cryo-specimens 130, which serves to avoid contamination from the cooling medium or from the environment. Typical dimensions of the specimen receptacles 123, for example, are 0.1 to 3 mm. The entire thickness of the storage substrate 100 amounts to approximately 2 mm, for example.

For the inventive cryo-storage of specimens, a storage substrate 100 (without the cover film 114) is first loaded with the cryo-specimens and reference specimens, if necessary. The loading takes place, for example, with a micro-drop shooting device, such as that described in EP-B 0 804 073. The specimens are shot as micro-drops in a cooled state of the storage substrate 100, aimed at the specimen receptacles 123, where, upon impingement, they freeze. Likewise, in a deeply cooled state of the storage substrate 100, writing (for example, a burning) of a first specimen data takes place in the specimen data storage 122. After loading of the substrate, the application of the cover film 114 and the insertion of the storage substrate in a support under the respective cooling conditions of the cryo-preservation system that is utilized take place.

Figure 2:
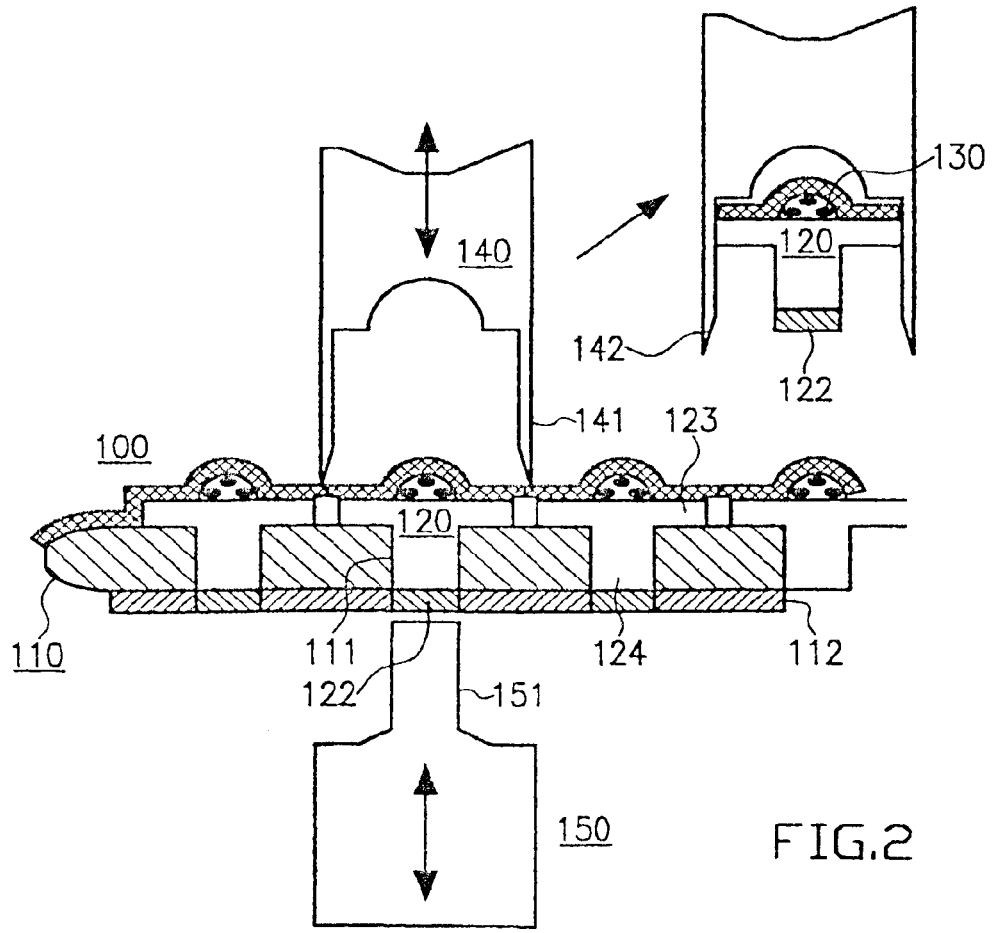
FIG. 2 is a schematic illustration of a specimen removal from a storage substrate according to FIG. 1.
Figure 3:
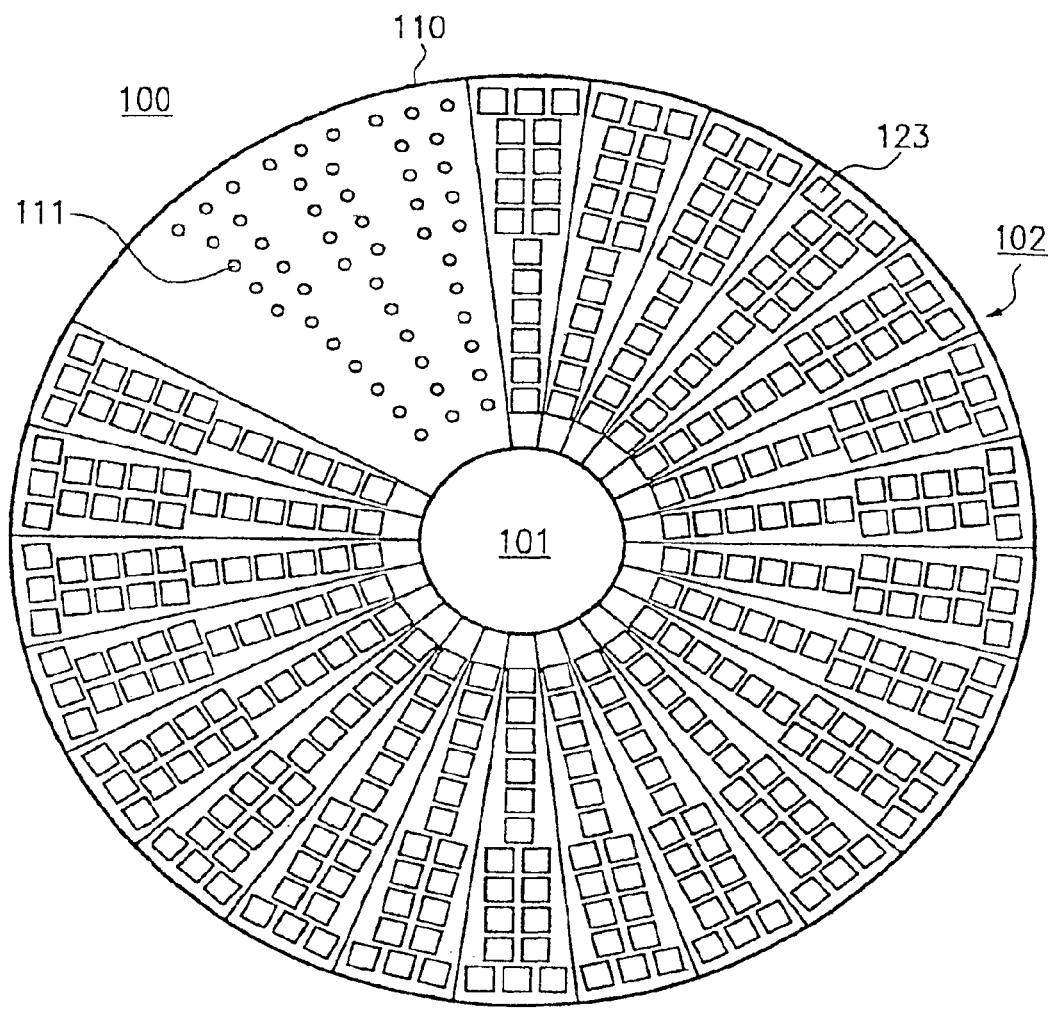
FIGS. 3 through 7 are schematic plan views of various forms of specimen and storage arrangements on a storage substrate.

In FIG. 2, the removal of specimens from the storage substrate 100 is illustrated. According to the present invention, the specimen removal takes place by separating the respective cryo-storage element 120 from the base body 110. The separation takes place with a cutting device 140 in cooperation with a punching device 150. The cutting device has a hollow cutting tool 141, whose blade is adapted to the outer shape of the specimen receptacle 123. The cutting tool, for example, can be formed as a hollow capillary with a ground end. The punching device 150 comprises a punch 151, with which the specimen data storage 122 is separated from the remaining storage medium 112 and the carrier pin 124 can be pressed out of the passage opening 111. On the end of the punch 151, if necessary, also a cutting tool for improved transection of the storage medium 112 is provided. The cutting and punching devices 140, 150 can be actively or passively cooled for maintaining a predetermined temperature of the storage substrate 100.

FIG. 2 shows a particular advantage of the invention. With the cutting device 140, the specimen 130 is removed with the cryo-storage element 120, without opening the other specimen deposits. The specimen 130 is also connected with the specimen data storage 122 after the removal. A transfer of the specimen to another storage substrate and/or a measurement device under cryo-conditions or with increased temperature can take place. A supplement of specimen data, for example, in dependence on a measurement result, is provided on the specimen data storage 122 (data accumulation).

FIGS. 3 through 7 illustrate inventive storage substrates (for example, according to FIG. 1) in schematic plan view. A storage substrate 100 is formed like a conventional CD and has in the center, in particular, a passage opening 101 for mounting of the storage substrate in the cryo-preservation device and/or a reading/writing system. The specimen receptacles 123 of the specimen carrier are formed in this embodiment as rectangles. They have typical surface dimensions of approximately 0.1 to 30 mm$^2$. The specimen receptacles 123 are arranged in groups in sectors 102. Upon removal of specimens with the respective cryo-storage elements, the base body 110 remains back with the free passage openings 111.

Figure 4:
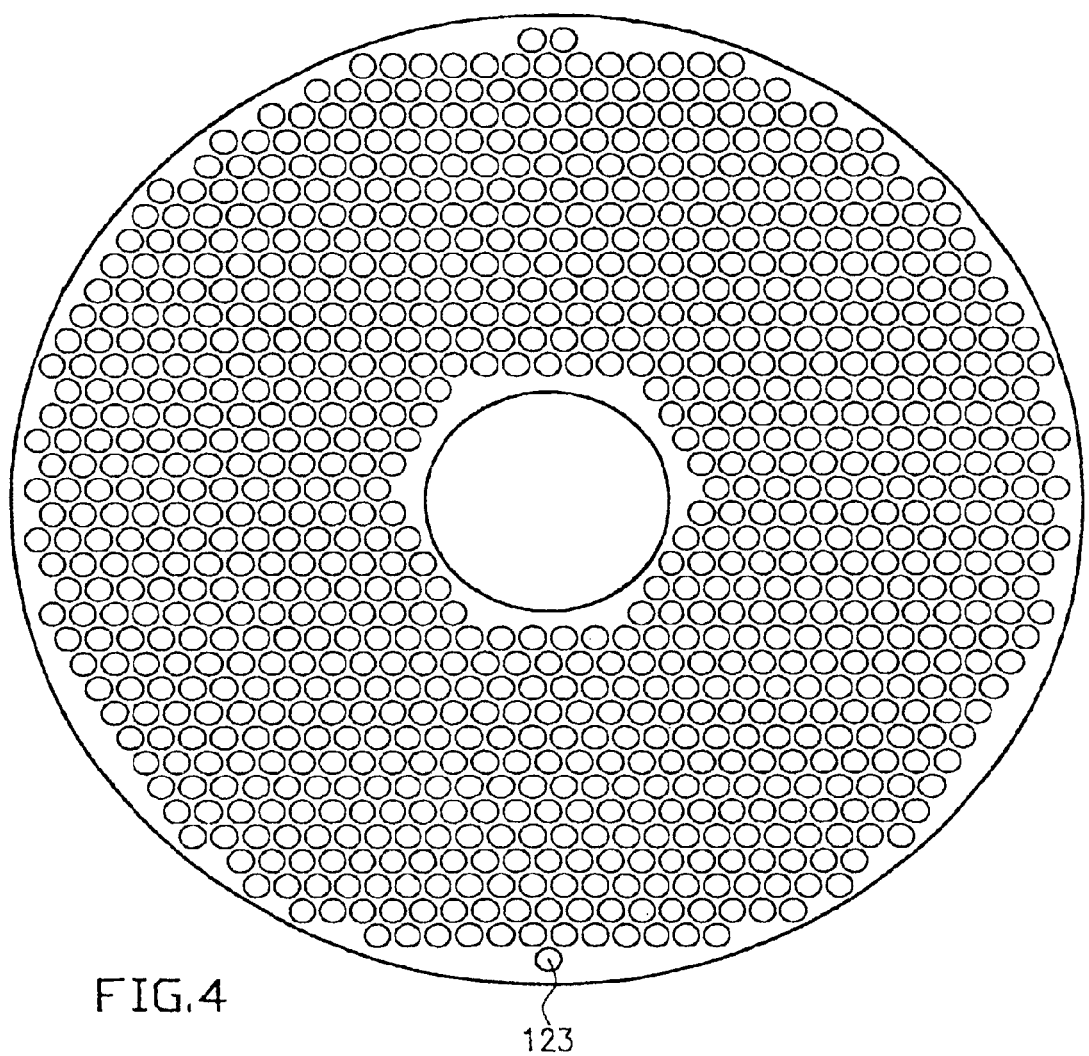

FIG. 4 shows a modified embodiment with circular specimen receptacles 123. On each specimen receptacle 123, a drop with a volume of some mm$^3$ can be stored. Each drop can contain up to $10^5$ cells. On the entire storage substrate with a diameter of approximately 12 cm, therefore, up to $10^8$ cells can be stored.

Figure 5:
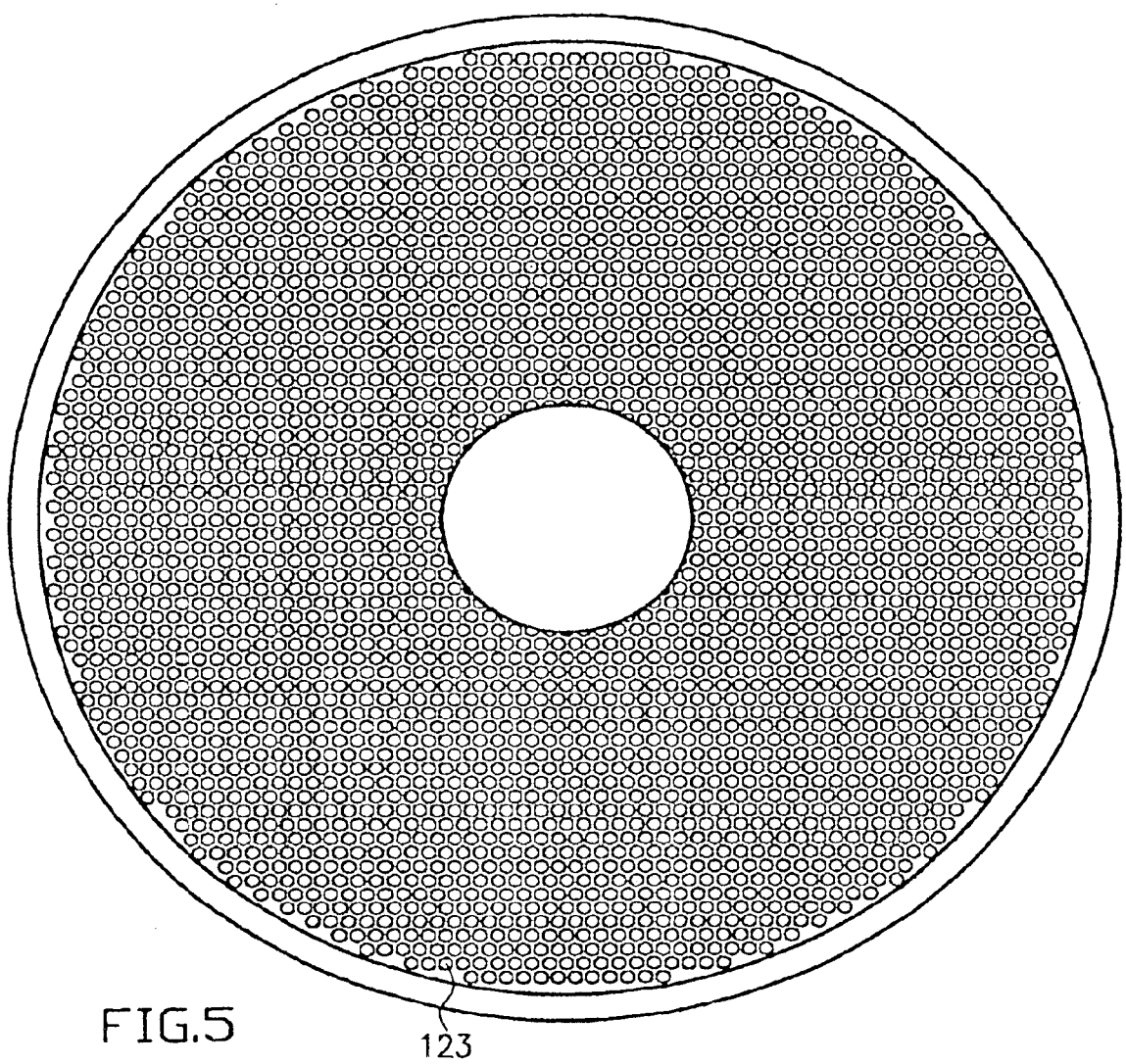

FIG. 5 shows a modified form with circular specimen receptacles 123, which, in comparison to FIG. 4, have smaller diameters (for example, 0.01 to 1 mm). The entire number of the cryo-storage elements on the storage substrate 100 is thereby increased. The variability increases with the specimen removal.

Figure 6:
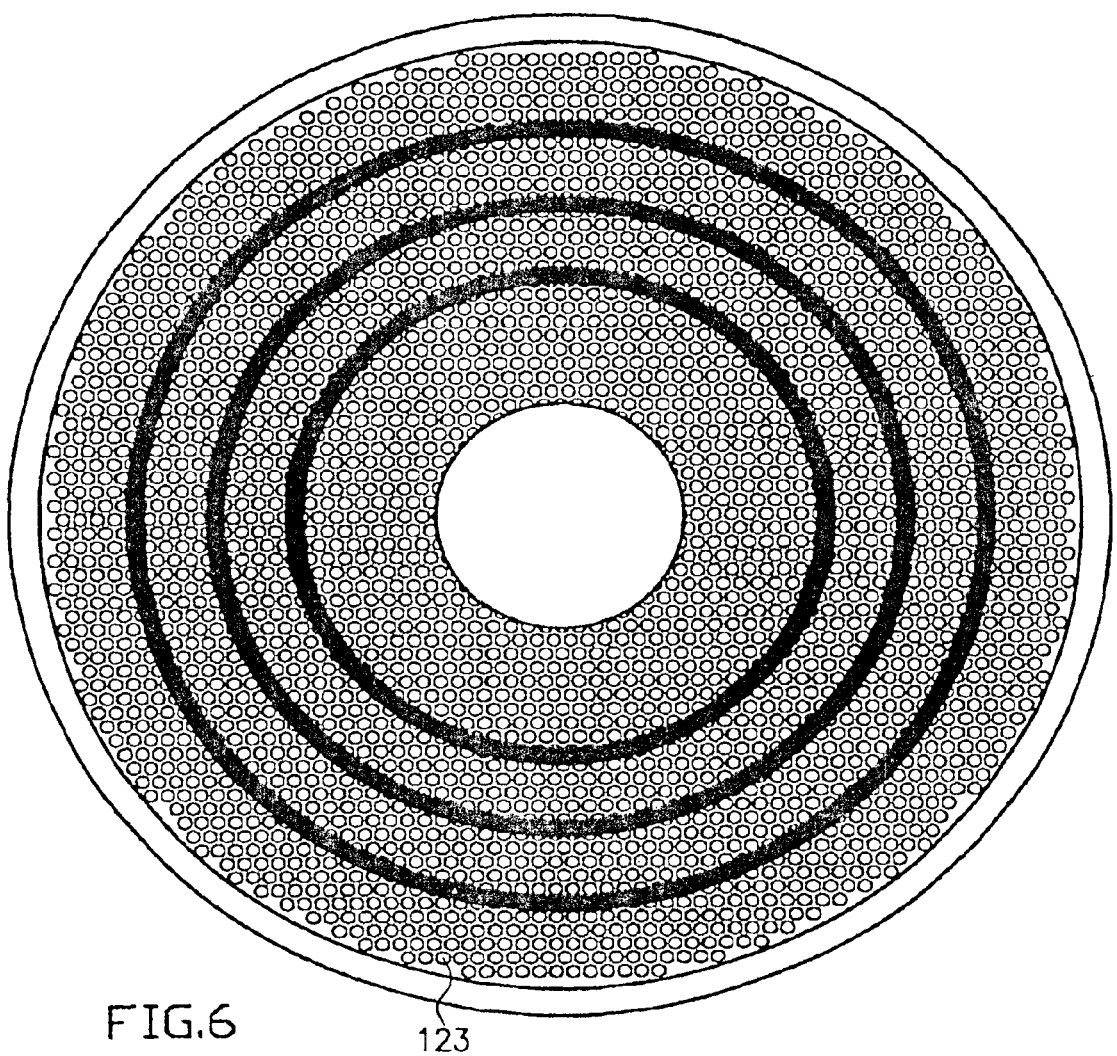
Figure 7:
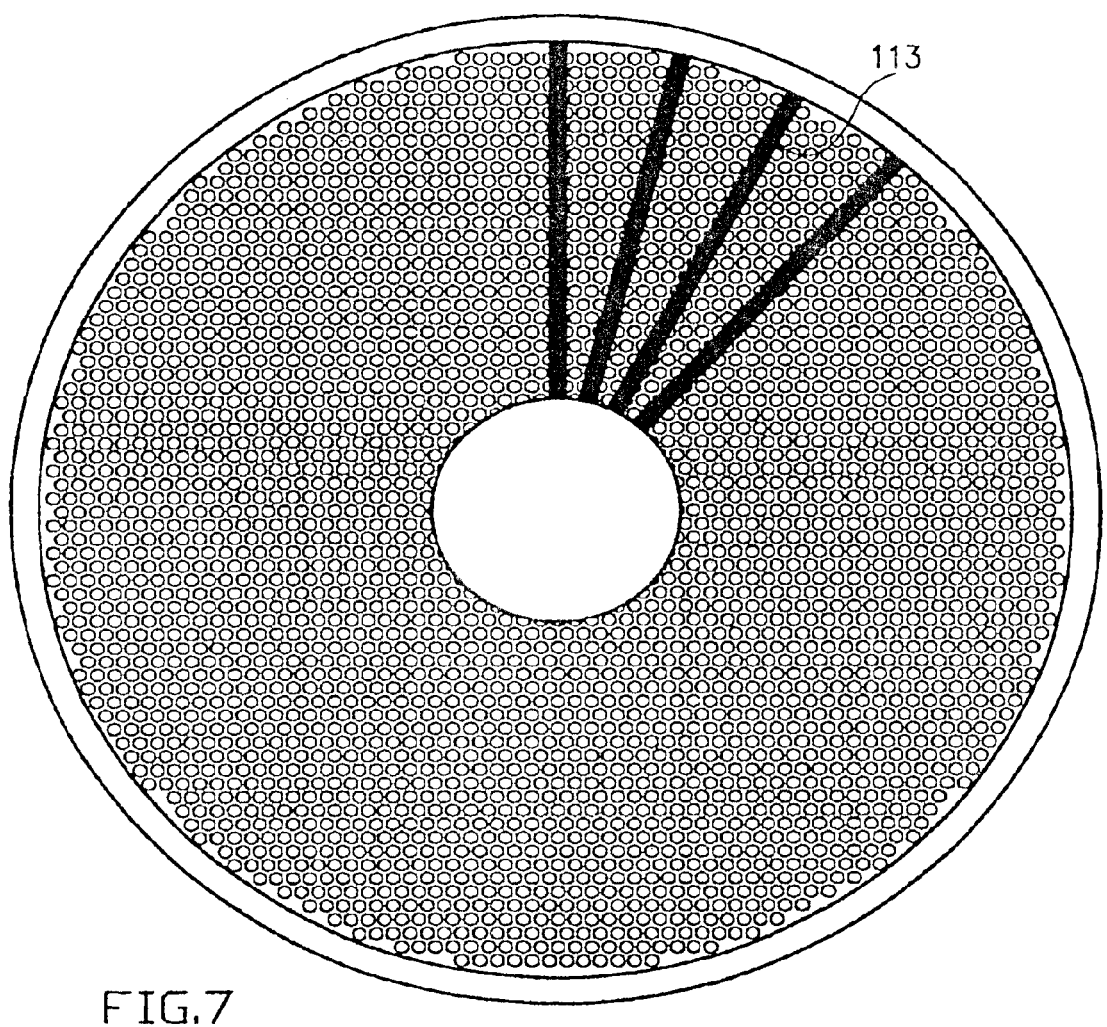

The base storage 113 illustrated in FIG. 1 can be arranged selectively according to determined channels in the storage medium. This is illustrated in FIG. 6 (ring-shaped storage channels) and 7 (ray-like, aligned storage channels). With the base storage 113, an additional fragmentation of the storage substrate takes place.

Figure 8:
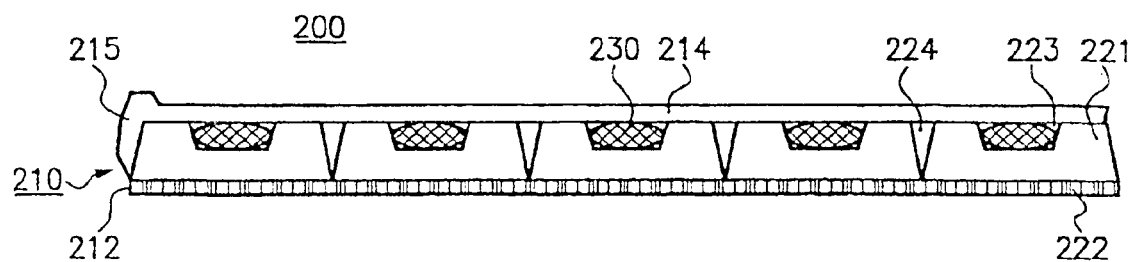
FIG. 8 is a schematic sectional view of a part of a storage substrate according to a second embodiment of the invention.

FIG. 8 illustrates in a cut-away manner a modified form of a storage substrate 200 with a base body 210, which is formed by the specimen carrier 221 of the cryo-storage element. The specimen carrier 221 has the specimen data storage 222 on one side and on the opposite side, the specimen receptacles 223. The specimen carriers 221 are formed components, for example, made of plastic or a semiconductor material, in which the specimen receptacles 223 are formed as recesses. The specimen carriers 221 are connected to one another via breaking points. The specimen data storage 222 forms a layer of the storage medium arranged on the underside of the base body 210. On the upper side of the storage substrate, a cover film 214 is provided, with which the specimens 230 are covered. The cover film 214 encompasses the base body 210 on its outer edge with a circulating projection 215.

The use of the storage substrate 200, in particular, the loading and the data storage, takes place according to the above-described principles. For data removal, cryo-storage elements 220 are separated respectively with a carrier 221 and a specimen data storage 222 with a suitable tool from the storage substrate 220 (for example, broken off, cut off, or the like). Depending on the application, the breaking points 224 are designed with a determined geometry, as illustrated in FIG. 9.

Figure 9:
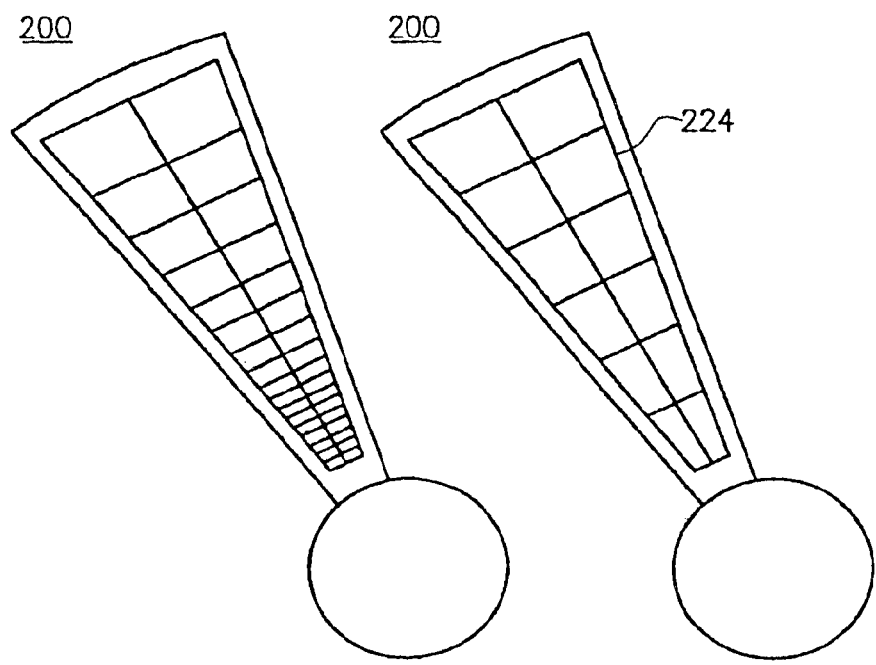
FIG. 9 is a schematic view of various geometric arrangements of cryo-storage elements.

In FIG. 9, the white lines designate the distribution of the breaking points 224. In the respective framed black regions, the specimen carriers, in particular, with the specimen receptacles, are arranged. The specimen receptacles can have various geometries within the storage substrate 200, for example, toward the interior, they can be more compact (left drawing part) or narrower (right drawing part).

Figure 10:
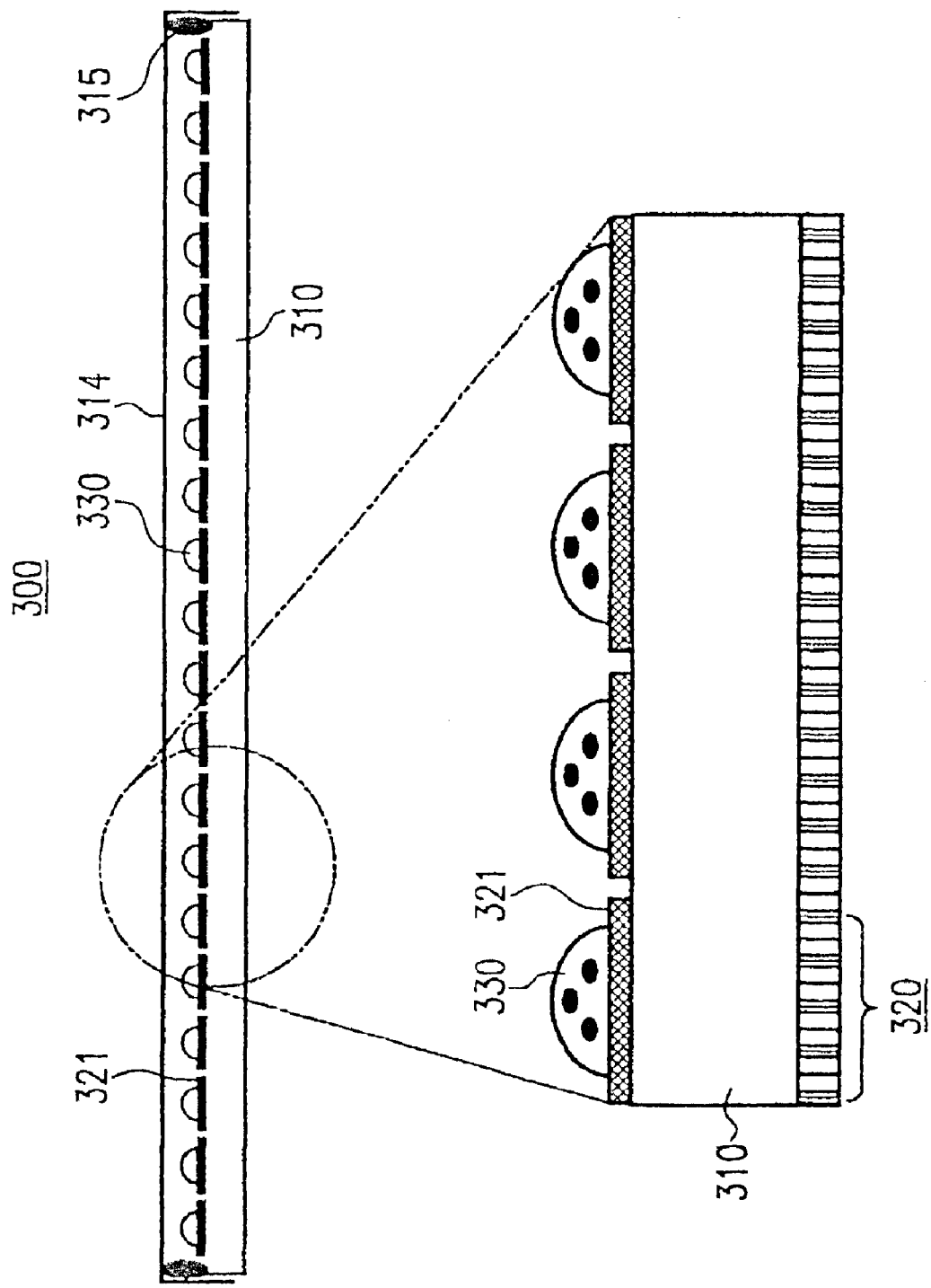
FIG. 10 is a schematic sectional view of a part of a storage substrate according to a third embodiment of the invention.

A third embodiment of the storage substrate 300 of the invention is illustrated in FIG. 10. The storage substrate has a disk-shaped base body 310 in the form of an even, uniform plate. Joints or breaking points are not provided in this embodiment. The cryo-storage elements 320 form merely one unit in this embodiment, as long as the specimens 230 are arranged on the storage substrate 300. As a specimen carrier 321, a specimen accommodation layer is provided for each specimen. The specimen accommodation layer comprises a plastic material, which has a minimal adhesive strength to the base body 310 (for example, made from PTFE or rubber). The minimal adhesive strength is provided, in particular, in low temperature ranges.

For separating a specimen 330, the specimen is separated with the specimen accommodation layer from the base body with a suitable tool (for example, detached, planed off, pushed off, or pulled off). The specimen data storage 322 remains on the substrate underside.

The specimens 330 are protected against contamination with a covering 314 in this embodiment. The covering 314 is formed by a cover, which is sealed against the based body 310 via an annular seal 315.

Figure 11:
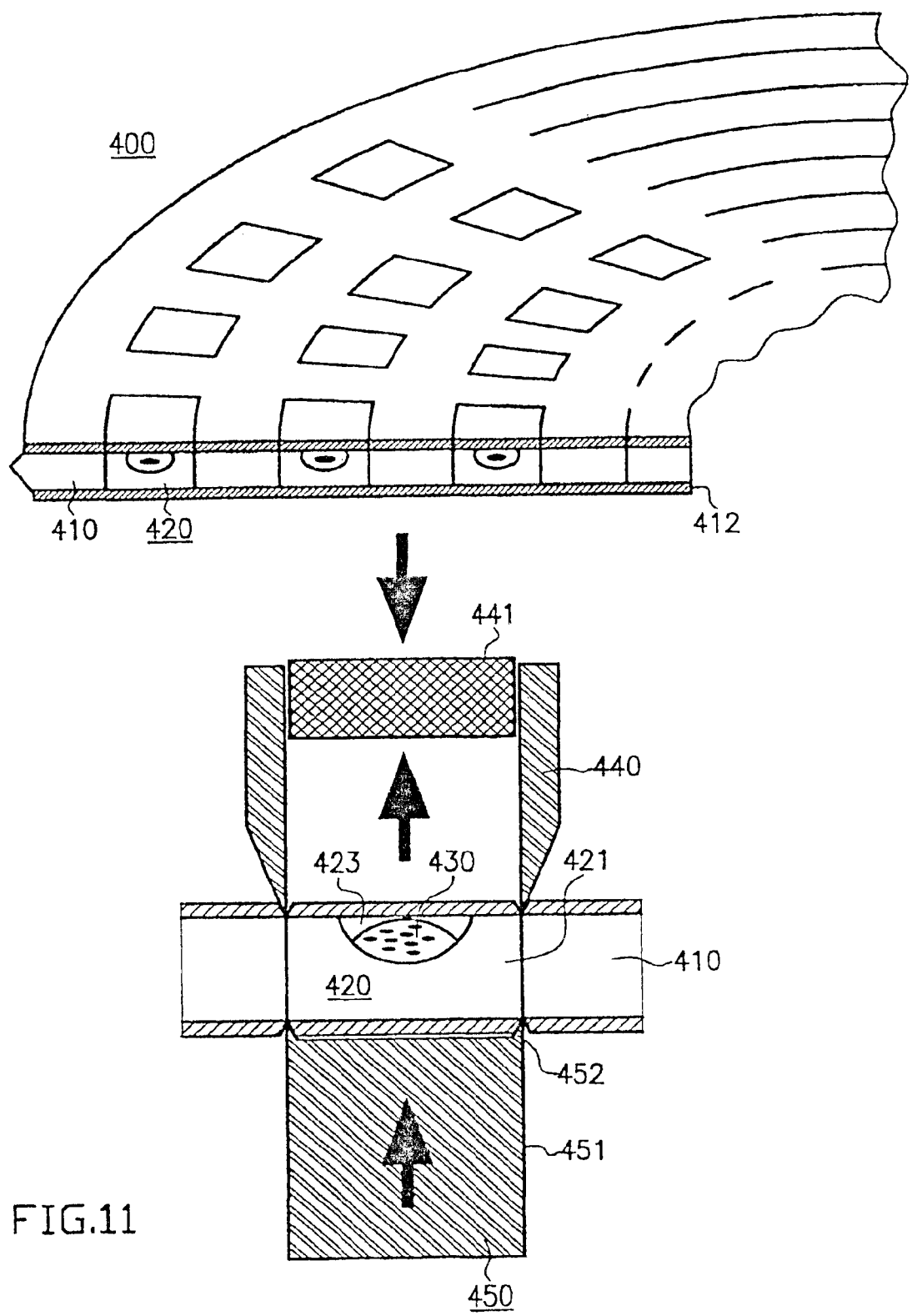
FIG. 11 is an illustration of the removal of cryo-specific elements from an inventive storage substrate according to a fourth embodiment of the invention.

In FIG. 11, in the upper drawing part in perspective view, a cut-away of a storage substrate 400 according to a further embodiment of the invention is shown. With this storage substrate, the cryo-storage elements 420 are provided in the form of a pre-perforation or a press-fit in the base body 410. The base body 410 and the cryo-storage elements 420 form a flat plate, on whose underside, the storage medium 412 is arranged as a layer. The storage medium 412 (data carrier film) likewise can be pre-perforated and is located on the underside of the base body 410 with the required planarity for optical reading-in and reading-out of data.

In the lower drawing part of FIG. 11, the cryo-storage element 420 is shown in an enlarged representation. On the top side of the base body 410, which here forms the specimen carrier 421, a recess is provided as the specimen receptacle 423. In the specimen receptacle, the cryo-specimen (for example, suspension drop) is arranged. With the cover film 414, the specimen 430 is protected against contamination. Also, on the cover film 414, perforations corresponding to the outer shape of the cryo-storage elements 420 can be provided. According to the invention, generally, the cover or cover film can be formed also as a storage medium. With removal of the cryo-storage element 420 from the storage substrate 400 with a tool formed analogously to the illustration in FIG. 2, the specimen 430 is removed with the specimen carrier 420, the specimen data storage 422, and the cut-out of the cover film 414.

The storage substrate 400 is fixed in a support and is separated from the base body 410 with the punch 451 (or with the blade 452, if necessary) and the cutting device 440. The cutting device 440 is provided with a movable punch 441, which, after separation of the cryo-storage element 420, presses this out of the cutting device.

Figure 12:
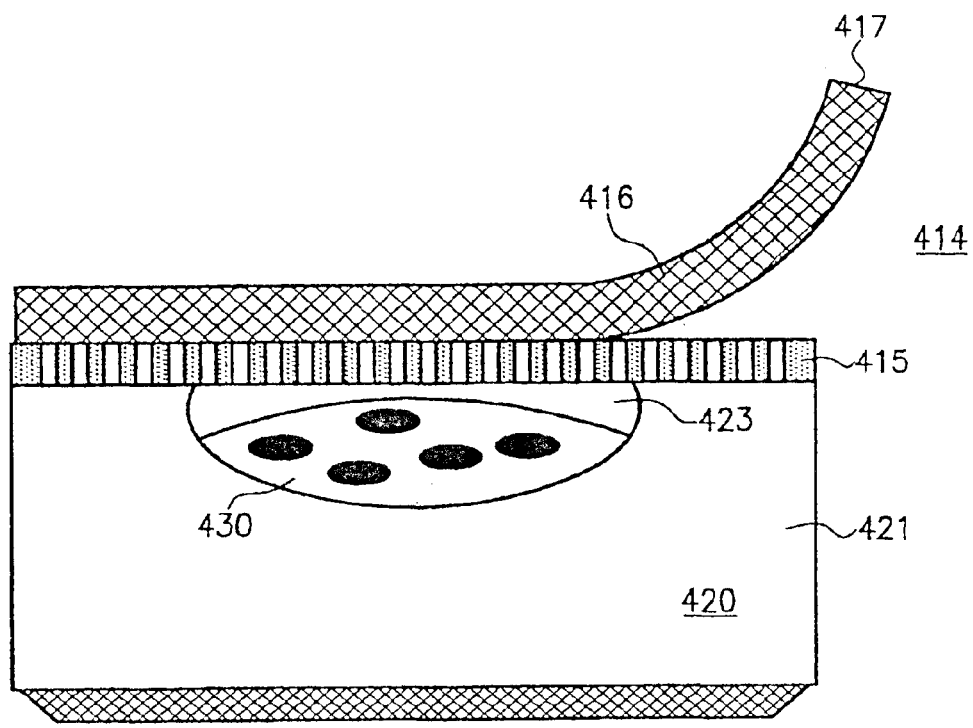
FIG. 12 is a schematic illustration of a film-like cover on an inventive storage substrate.

FIG. 12 shows a modification to the embodiment of FIG. 11, by way of example, of an individual cryo-storage element 420 with the specimen carrier 421 and the specimen receptacle 423. With this form, the cover 414 is formed as a two-layered film. A porous layer 415 overlies the specimen carrier 421 as a cover. Over that, a sealing layer 416 with an extension 417 extending up from the substrate plane is provided. The extension 417 can be pulled away from the substrate manually or with an appropriate tool. In this manner, the lower layer 415 on the specimen carrier 20 is laid open. This procedure can take place in a deep-freeze state or also in a thawed state. A quick exchange of the liquid in the specimen receptacle 423 can take place. For example, cryo-protective can be washed out of the cell suspension.

The cover 414 can also contain data or markings for identification of the specimen. According to modified forms, a further structure of the cover 414 formed as additional layers can be provided.

Figure 13:
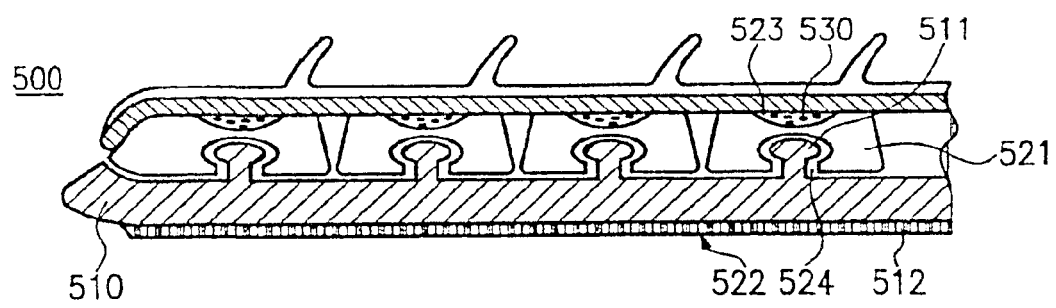
FIG. 13 is a schematic sectional view of a part of a storage substrate according to a fifth embodiment of the invention.

The principle of the multi-layered cover is also shown in FIG. 13 by way of an example of a further embodiment of the invention. There, the storage substrate 500 includes, in turn, a base body 510 with mushroom-shaped projections 511, on which the specimen carrier 521 sits. The specimen carriers 521 are formed components, respectively, with a specimen receptacle 523 on the upper side and a fixing recess 524 on the underside. The fixing recesses 524 and the projections 511 work together like push buttons as releasable mechanical connections. On the side opposite the specimen carriers 521, a data carrier layer as the storage medium 512 is located, which forms the specimen data storages 522 that are associated with respective specimen carriers 521. The covering 514 takes place according to the double-layer principle, which is illustrated in FIG. 12.

For removal of a specimen carrier 521 in a frozen state of the storage substrate 500, a planar or wedge-shaped tool is shoved under the specimen carrier 521. With the tool, the connection between the respective projection 511 and the fixing recess 524 is loosened. The specimen is thereby separated from the storage substrate 500 with the specimen carrier 521 and parts of the cover 514. Also with this embodiment, upon separating, the connection to the specimen data storage 522 is lost. But, specimen data also can be provided in appropriate parts of the cover 514.

The embodiment shown in FIGS. 14 through 26 illustrate that the storage substrate 600 is formed by means of at least one circuit board 610, which corresponds to the base body and on which one or more cryo-storage elements 620, like electrical circuits (chips) are arranged. The circuit board 610 supports electrical (conducting paths) or optical (photoconductor fibers) connections 611, which connect, respectively, a receptacle mounting 612 for receiving a cryo-storage element with an external control device (not shown). The receptacle mounting corresponds essentially to a socket of a conventional circuit mounting, in which the contacts of the cryo-storage element (see, for example, FIG. 15) are used. On the receptacle mountings 612, additional circuits for signal modulation, signal conversion, or detection of the data signals running from the connection lines 611 or from the optical path can be provided.

Figure 14:
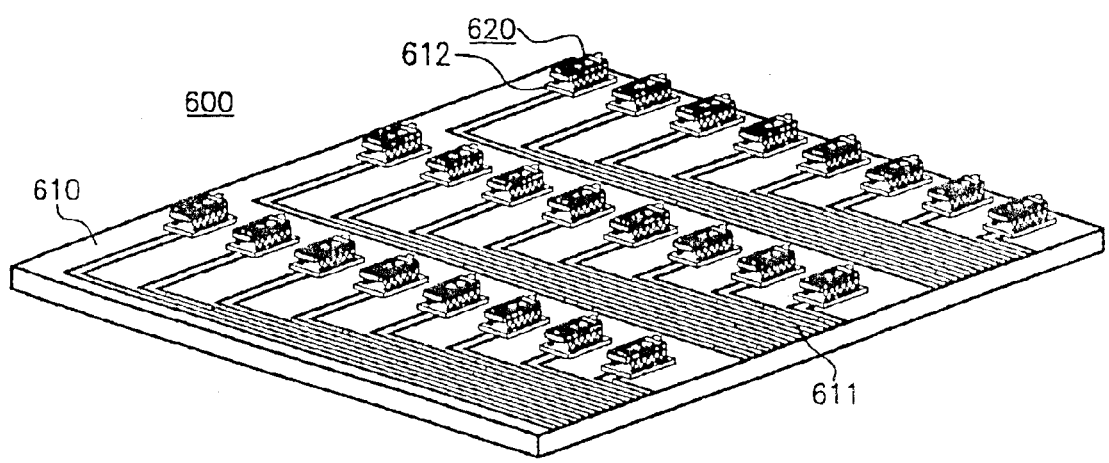
FIG. 14 are schematic perspective views of storage substrates according to a sixth embodiment of the invention.
Figure 14:
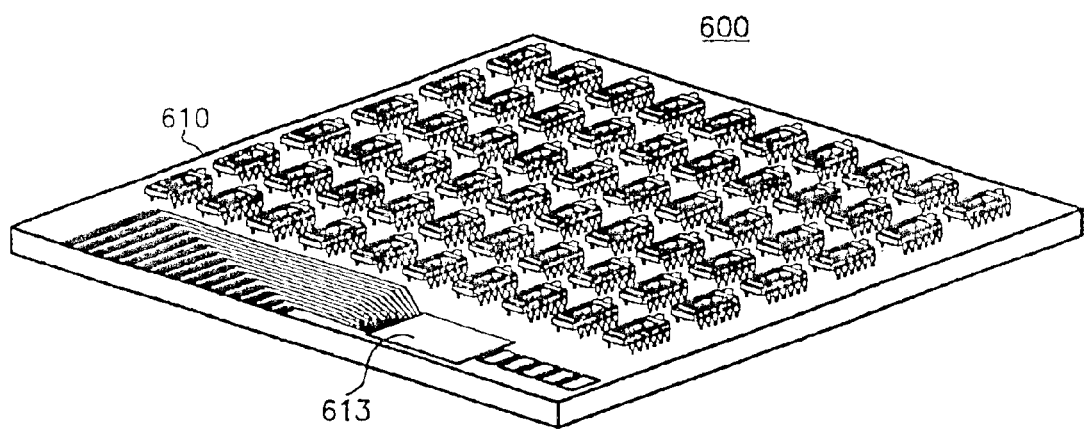

The connecting lines 611 can be provided on the top side of the circuit board 610 with the receptacle mounting 612 (upper drawing part of FIG. 14) or on the opposite side (lower drawing part of FIG. 14). In the last case, the receptacle mountings 612 are more tightly arranged. The lower drawing part of FIG. 14 shows further than on the circuit board 610, also a computing circuit 613 for control of the cryo-storage elements, with the required RAM storage, if necessary, can be provided.

Each receptacle mounting 612 is equipped for receiving a cryo-storage element 620. Each cryo-storage element 620 includes a specimen carrier 621, analogous to the above-described function, which is connected with the specimen data storage 622. According to a particular advantageous embodiment of the invention, the cryo-storage element is formed by an integrated circuit (for example, storage components) known as such. The circuit contains as the specimen data storage 622 at least one RAM storage. The cryo-storage element 620 also can contain a complete computing circuit, with which the function of the cryo-storage element is executed and by means of which the cryo-storage element communicates externally. The specimen carrier 621 preferably is formed in or in connection with the plastic covering or encapsulation of the integrated circuit.

Figure 15:
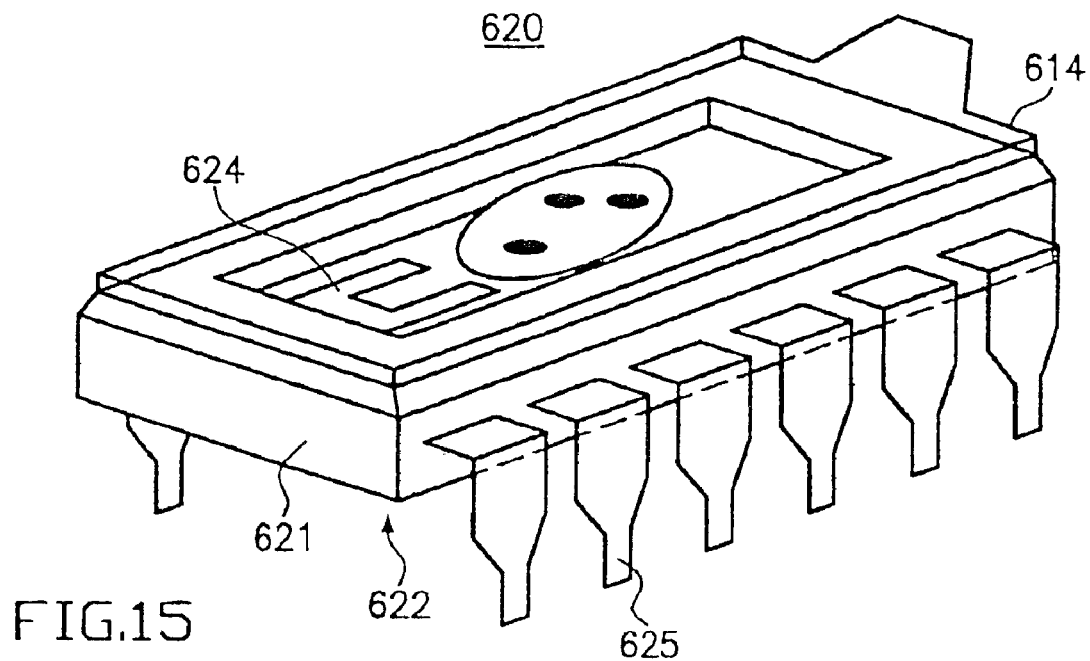
FIG. 15 is a schematic perspective view of a cryo-storage element of the storage substrate according to FIG. 14.

The specimen receptacle 623 is, for example, a recess in the plastic over as shown in FIG. 15. With a conventional chip with a size of 7·14 mm, the specimen receptacle 423 can have a base surface of approximately 4·10 mm with a depth of 1 mm. With these measurements, up to five million cells can be accommodated in the cryo-storage element 620.

On the bottom of the specimen receptacle 623, additional control devices for manipulation of the specimen sensor and/or display units 624 can be provided. The control devices include, if necessary, cooling and heating elements, for example, peltier elements, resistance heating elements for controlling cooling or heating of the specimen, or materials with increased heat capacity for reduction of the heat load of the specimen during a chip transport. As a display device, a light source can be provided, which, for example, signals a predetermined state of the cryo-storage element 620 or the specimen, or which serves as a measured light source for measurement on the specimen 630. In addition, the cryo-storage element 620 is provided with a cover 614, which protects the specimen from contamination, evaporation, and sublimation. The cover 614 is a plastic cap, for example, a welded-on film, or another layer-type component, which provides a sealed, releasable connection with the specimen carrier 621.

The specimen carrier 621 serves also as a guide for the contact connectors 625 of the cryo-storage element. The contact connectors are connected, in particular, with the specimen data storage 622 and, if necessary, to the control and display devices 624.

In contrast to the diagnosis chips known from cellular biotechnology, with the cryo-storage element 620, no connection exists between the specimen 630 and the specimen data storage 622, the control and/or display devices 624, which is directed to a detection of electrical parameters of the cells frozen in the specimen.

Figure 16:
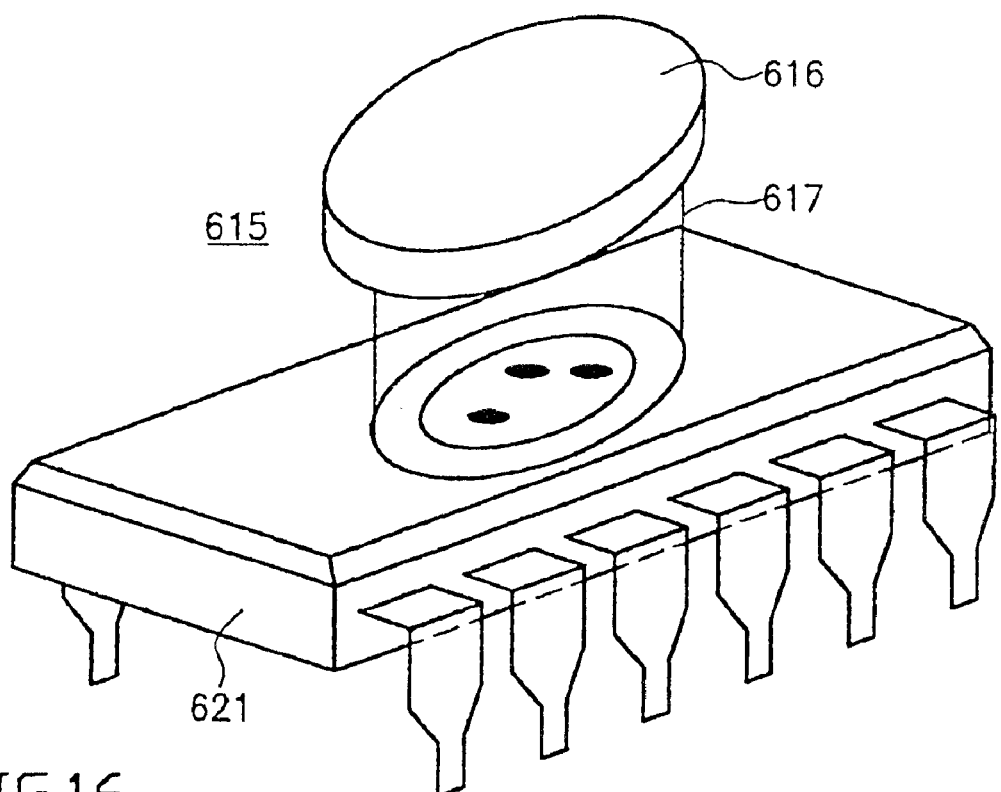
FIG. 16 is a schematic perspective view of a modification of the cryo-storage element according to FIG. 15.

The cover 614 according to FIG. 15 can also be replaced with a cryo-container 615, according to FIG. 16. With the cryo-container 615, the top side of the specimen carrier 621 is provided with a sealed screw connection to a cylindrical container body 617. The cryo-container 615 comprises a cold-resistant plastic material. The embodiment of the invention shown in FIG. 16 has the advantage that the cryo-container 615 can also be loaded manually, for example, by means of pipettes.

Detailed further embodiments of the inventive cryo-storage elements 620 are shown in FIGS. 17 through 26. The cryo-storage element 620 according to FIG. 17 includes a specimen carrier 621 and a specimen data storage 622. The specimen data storage 622 is structured like a known electronic storage chip with contact electrodes 625 and an encapsulation 626, in which a storage circuit and, if necessary, a computing circuit are arranged. The encapsulation 626 comprises typically a plastic material.

The specimen carrier 621 is attached to the top side of the encapsulation 626 or as part of the encapsulation 626. The specimen carrier 621 comprises a plastic frame 627, in which for receiving specimens, at least one cryo-container 615 is integrated. The plastic frame 627 is an injection molded part with a size corresponding to the surface of the encapsulation 626, for example. The lateral frame parts are provided with bores, in which the cryo-containers 625 are arranged.

Each cryo-container 615 forms at least one elongated specimen chamber. The at least one specimen chamber has an elongated form, such that the inner cross section is essentially smaller than its length. As specimen chambers, for example, hoses, hollow needles, capillaries, or the like are provided. The internal diameter of a specimen chamber lies in the range of 5 $\mu$m to 4 mm, for example. The length can be chosen to be in the range of 0.5 cm to 10 cm. The quotient of the cross sectional diameter and length of a specimen chamber is preferably smaller than $\frac{1}{10}$. The allocation of at least one cryo-container 615 in a tube or hose form has the advantage of a fast loading or emptying of the specimen chambers, a high ability for miniaturization, and a high freezing speed.

Figure 17:
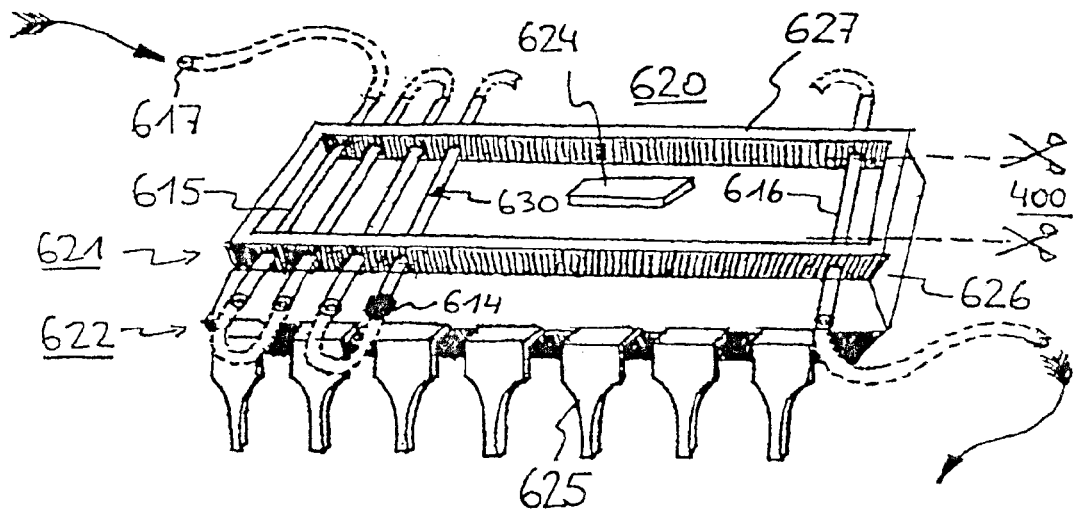
FIGS. 17 through 20 are schematic perspective views of the inventive cryo-storage element according to further embodiments of the invention.
Figure 18:
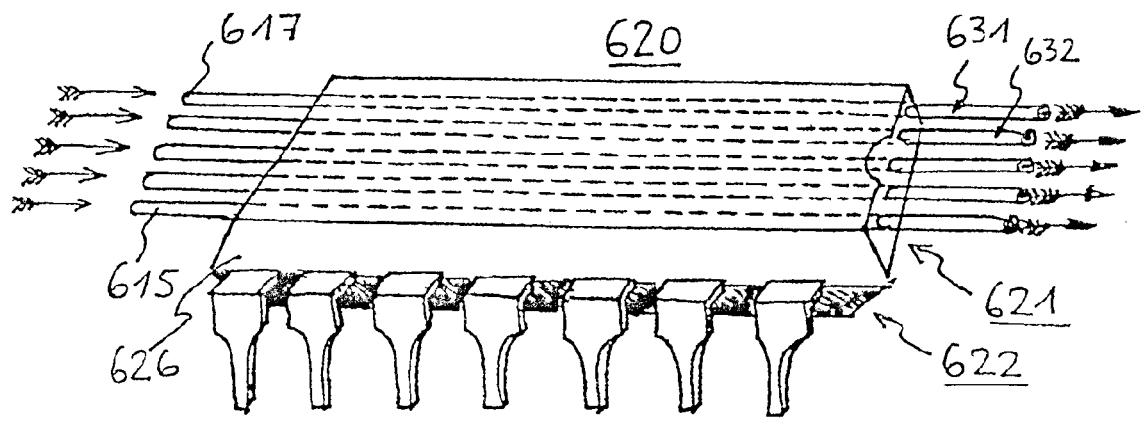

With the embodiment of the invention illustrated in FIG. 17, first a cryo-container 615 is formed by a meander-shaped hose placed in the frame 627 (partially shown). After loading of the cryo-container 615 via the hoses (see arrow), the parts of the hose designated with dashed lines are cut off, so that the sections drawn through remain as separated cryo-containers (for example, 616). All cryo-containers 615 are loaded as a unit with a common specimen 630, which advantageously is subdivided into specimen parts. With a mechanical separating device 400, the specimen parts 616 can be separated from the cryo-element 620 in a frozen or thawed state, without affecting the remaining specimen parts.

On the surface of the encapsulation 626 and/or on the frame 627 of the specimen receptacles 623, additional control devices for manipulating of the specimen and/or the sensor and/or the display units 624 can be provided. The control devices include, if necessary, cooling and heating elements, for example, peltier elements, resistance heat elements or the like. They serve for the controlled cooling or heating of the specimen or materials with increased heat capacity for reducing the heat load of the specimen, for example, during a chip transport. The sensor and/or display can have a light source, which signals, for example, a predetermined state of the cryo-storage element 620 or the specimen or serves as a measured light source for measurement on the specimen 630.

In addition, each end of a cryo-container 615 can be provided with a cover 614, which protects the specimen from contamination, evaporation, and sublimation. The cover 614 is, for example, a plastic cap, a welded-on film or another component, which provides a sealed connection with the ends of the respective cryo-container 615. If a hose if provided as a cryo-container, then the cover can be formed also by means of a part of the hose itself, which is clamped together on its ends.

Instead of a through-going and, if needed, cut hose, according to FIG. 17, also a plurality of tube-shaped cryo-containers 615 made from a rigid material can be provided as specimen receptacles 623, which are aligned transversely (FIG. 17) or parallel (FIG. 18) to the longitudinal orientation of the cryo-element 620. With the embodiment according to FIG. 18, for example, five cryo-containers 615 are integrated in the encapsulation 626 (enclosed). This can take place by injection of the cryo-container 615 into the encapsulation material or an adhesive bonding. The cryo-containers 615 are formed by hollow needles or capillaries.

The loading of a cryo-container 615 takes place, in which on one end, a low pressure exists and via the opposite input end 617, the cryo-specimen is received. Instead of applying low pressure, also a specimen receptacle can be provided with the action of capillary forces in the interior of the cryo-containers 615. In particular, with the embodiment according to FIG. 18, the same or different cryo-specimens 631, 632, . . . , can be accommodated in the individual cryo-containers 615. The cryo-containers 615 are preferably spaced from one another, such that the feeding ends 617 are aligned to correspond to the format of a micro- or nanotiter plate.

Figure 19:
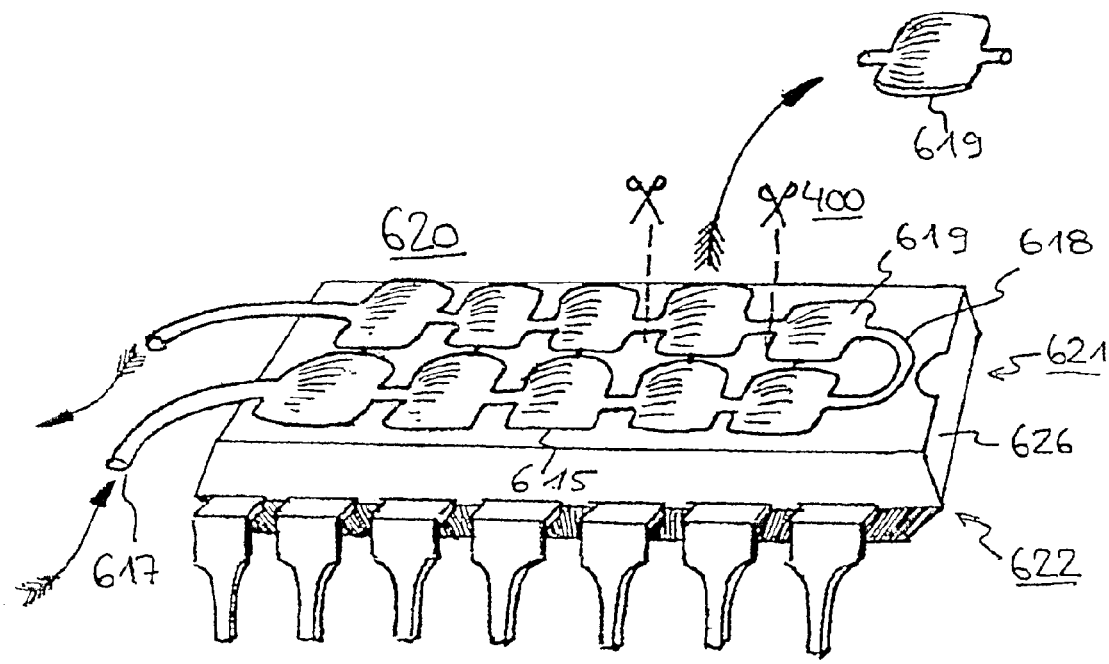

According to an alternative embodiment of the inventive cryo-element 620 illustrated in FIG. 19, the cryo-container 615 of the specimen carrier 622 is formed as a hose, whose diameter in the longitudinal direction of the hose is changeable. Sections 618 change with a small diameter and chamber parts 619, in which the hose is considerably widened. The cryo-container 615 includes a plurality of chamber parts 619, which advantageously, can be separated from the cryo-element with a mechanical separating device 400. The cryo-container is attached on the encapsulation 626 of the specimen storage 622 (for example, adhered or partially injected). The loading of the cryo-container 615 takes place under formation of a low pressure, which is absorbed via the input end 617 in the suspended cryo-specimen in the cryo-container 615.

Figure 20:
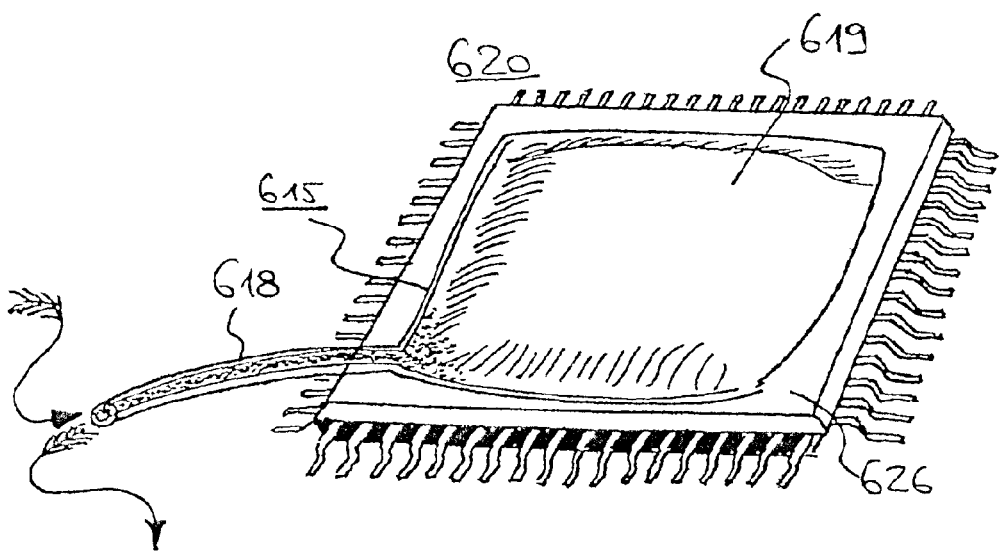

According to FIG. 20, the cryo-container 615 also can be formed from a hose, which has only one chamber part 619, which, as shown, is loaded or emptied via a hose section 618 or alternatively, via multiple hose sections. The chamber part 619 according to FIG. 20 is formed from a film material, which is adhered on the encapsulation 626.

In contrast to the diagnosis chips known from cellular biotechnology, with cryo-storage elements 620, no connection exists between the specimen 630 on the one hand, and the specimen data storage 622 and/or the control, sensor, and/or display devices 624, on the other hand, which is directed toward a determination of electrical parameters of the cells frozen in the specimen.

Figure 21:
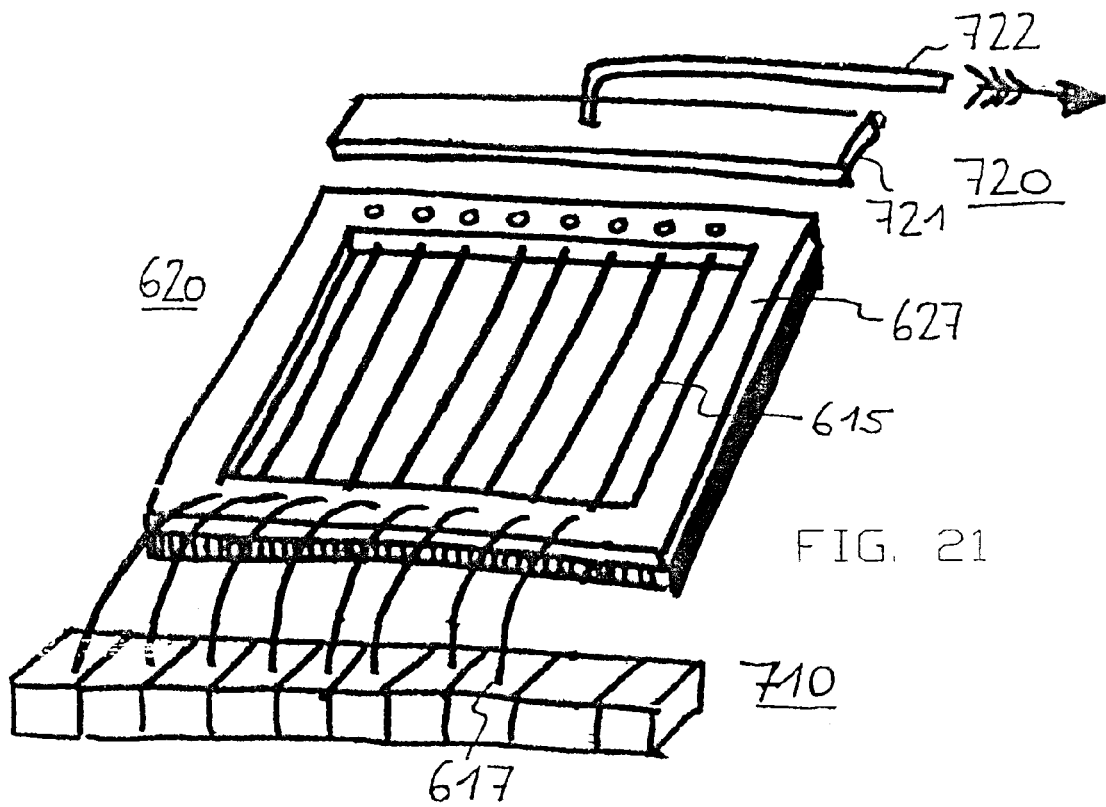
FIGS. 21 and 22 are schematic illustrations of the loading of the specimen carriers and the removal of the specimens.
Figure 22:
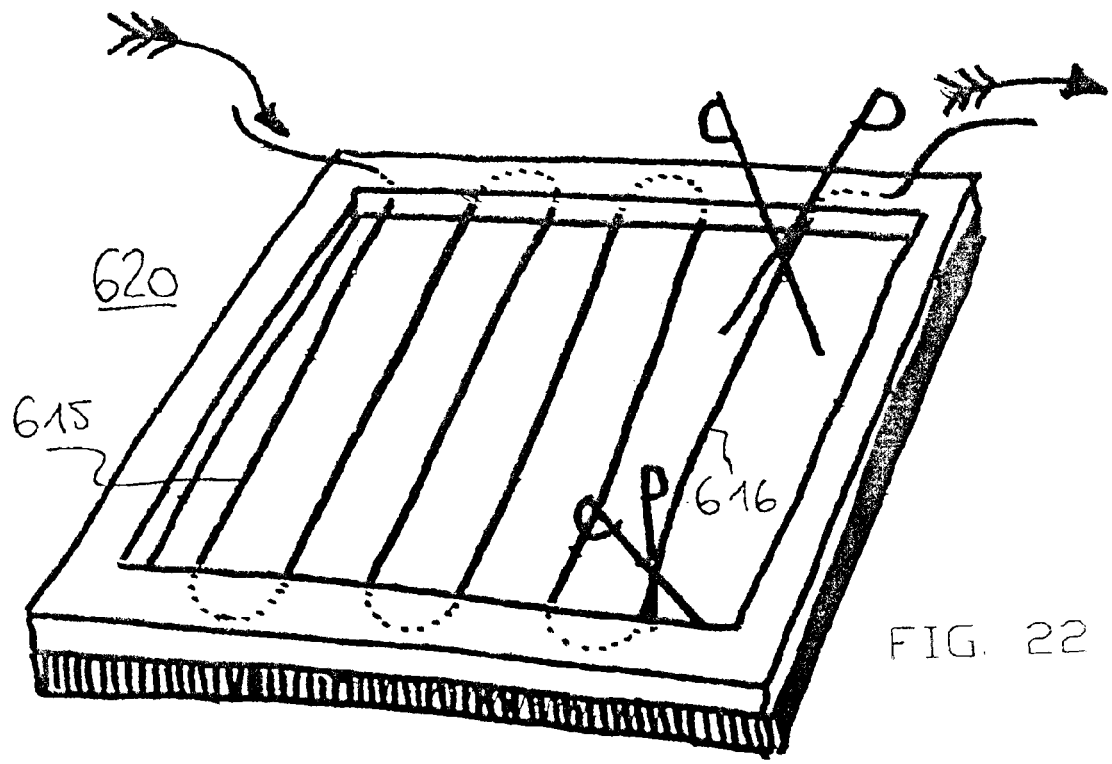

In FIGS. 21 and 22, further details of the loading and the specimen removal from cryo-elements 620 are illustrated. The loading takes place according to FIG. 21, for example, with a loading device, which on one side, has a plurality of specimen reservoirs 710, and on the other side, has a pressure device 720. The cryo-storage element 620 includes a frame-type specimen carrier 621, analogous to the embodiment shown in FIG. 17, on which a plurality of cryo-containers 615 in the form of capillaries or hoses are arranged, whose feeding ends 617 project into the specimen reservoir 710. The specimen reservoirs 710 are reservoirs, in which specimens are located after extraction of a specimen. The pressure device 720 includes a pressure attachment 721, which can be placed in pressure-tight manner on the opposite ends of the cryo-container 615, and a connection line 722, via which all cryo-containers 615 can be pressurized with low pressure. The ends of the cryo-container 615 are preferably mounted for common receipt of the pressure attachment 721 on a frame part. They can, for example, open into the surface of the frame 627. Under the action of the low pressure, specimens 630 are accommodated into the cryo-container 615.

After the loading of the specimen carriers 621, the cryo-storage element 620 is separated from the loading device. The input ends 617 are shortened, if necessary, to the frame 627. The cryo-storage element 620 is placed on a storage substrate 610 (see FIG. 14), and with this, is transferred in an environment with a reduced temperature, for example, a cryo-container in a cryo-bank.

In FIG. 22, one possibility of specimen removal from a cryo-storage element 620 with a meandering-designed cryo-container 615 is illustrated. The specimen parts 616 are separated with a mechanical separating device 400, for example, a cutting device. This can take place advantageously in a state of reduced temperature, so that the remaining specimens can remain unchanged.

Figure 23:
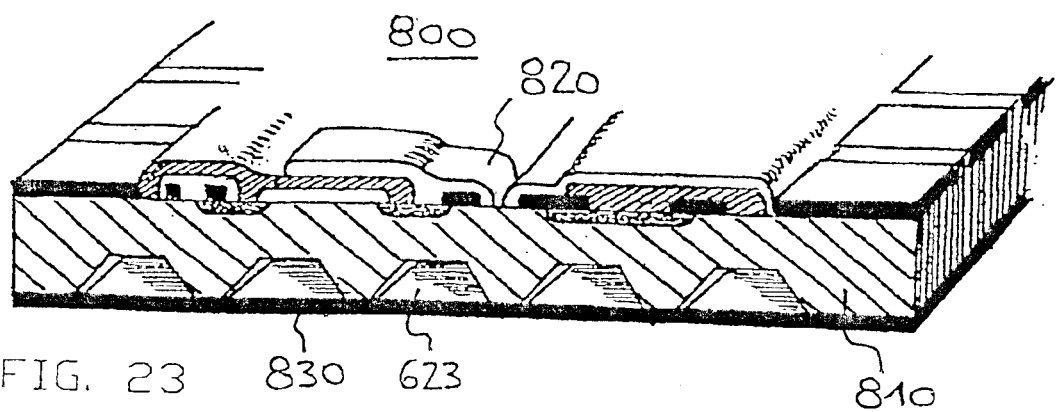
FIGS. 23 through 26 are schematic perspective views of the inventive storage substrate according to further embodiments of the invention.

In FIGS. 23 through 26, embodiments of the inventively used cryo-storage elements 620 are shown, which, in contrast to the above-described embodiments of the specimen holder 621, is integrated not in an encapsulation of the storage circuit, rather in its substrate material. FIG. 23 shows, for example, a part of a cryo-storage element 620 (without encapsulation and without contact connector). A storage circuit 800 with a substrate 810 and integrated components 820 are shown in sections. The substrate is a semi-conductor wafer, for example, as are commonly used for manufacturing of integrated circuits. On the upper side of the substrate 810, the components 820 are processed with a known method of semi-conductor technology. On the underside of the substrate 810, channel-like specimen chambers 623 are formed as specimen receptacles, which are closed with a cover layer 820. The specimen chambers 623 have measurements of 400 µm, for example (cross sectional dimension) and 20 mm (length). The specimen chambers 623 can also be formed in a structured substrate layer, which is arranged on the substrate (see FIG. 24). The cover layer 830 comprises a plastic material, glass, or a semiconductor material.

Figure 24:
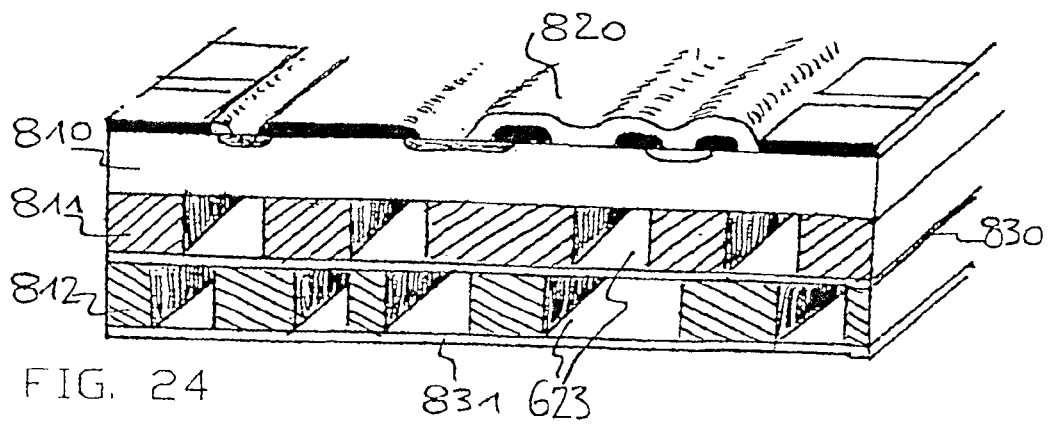

In addition, multiple levels with specimen chambers 623 can be provided, as illustrated in FIG. 24. On the substrate 810, a first structured substrate layer 811 with specimen chambers 623 and a first cover layer 830 can be provided. On the first cover layer 830, at least one further structured substrate layer 812 with specimen chambers 623 and a further cover layer 831 can be provided. With this embodiment, advantageously, an enlarged specimen volume on the associated specimen data storage is absorbed. The filling or specimen absorption on the cryo-storage elements 620, according to FIGS. 23 and 24, takes place via hose connections, which are integrated in the encapsulation of the specimen data carrier 622 and are cut off or pinched off after use.

Figure 25:
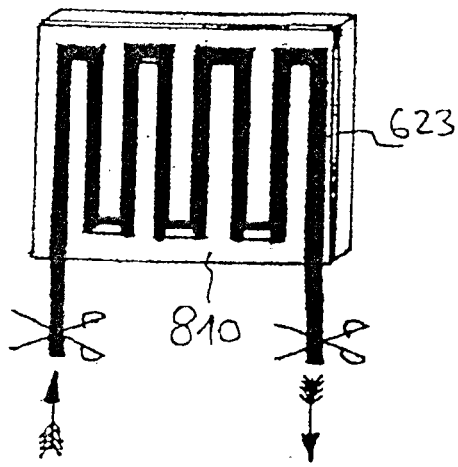
Figure 26:
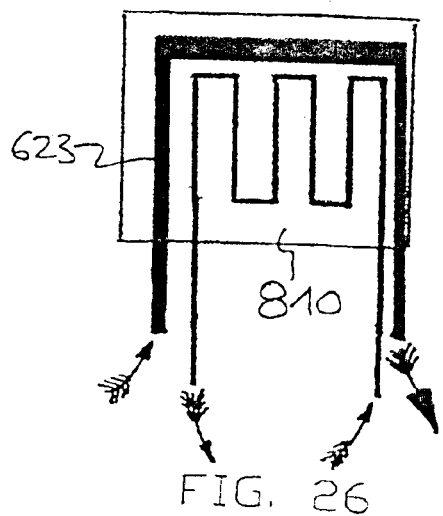
Figure 27:
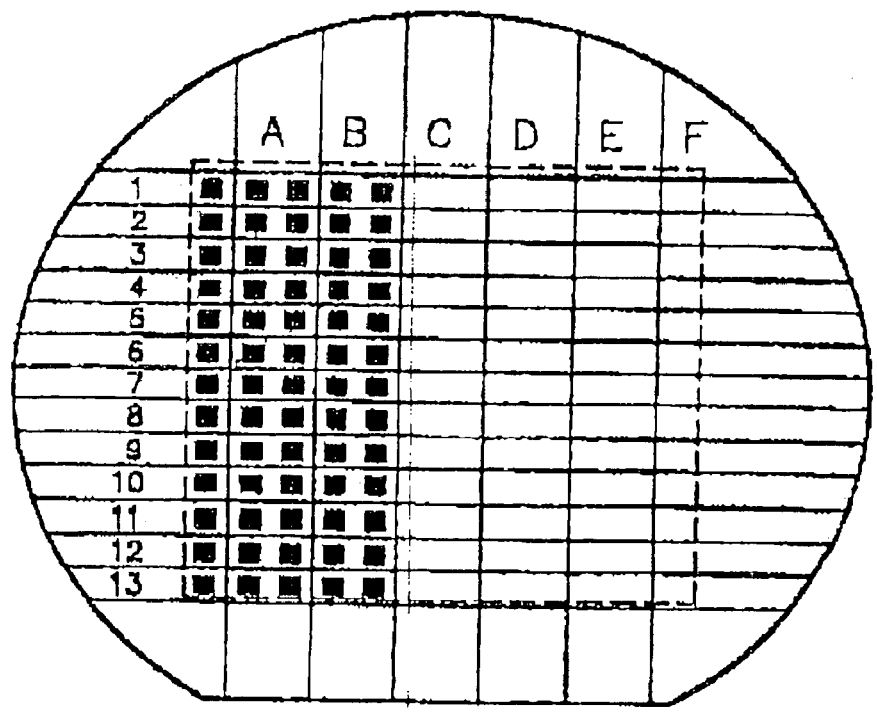
FIGS. 27 and 28 are plan views of conventional specimen carriers (prior art).
Figure 28:
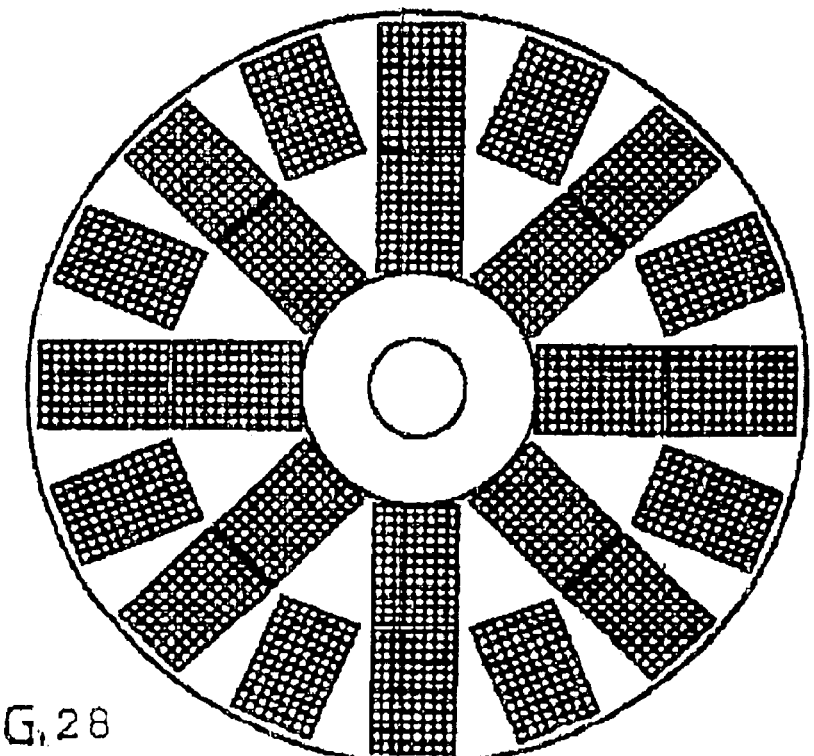

In FIGS. 25 and 26, various geometries of the channel-shaped specimen receptacles 623 in the substrates 810 are schematically illustrated. For example, meandering or U-shaped channel shapes with various cross sectional dimensions can be provided, which, if necessary, are arranged nested in one another.

The embodiments of the invention shown in FIGS. 14 through 26 have a series of advantages. The cryo-storage element is formed by an electronic chip, which contains an electronic storage that is externally writable and readable as the specimen data storage. A temperature-dependent adjustment of a reading/writing head, like that in a CD storage, is not necessary. In the chip, at least one specimen receptacle corresponding to one or more specimens is located. The chip and/or the receptacle mounting can be equipped with an electronic switch for controlling additional functional elements, sensors, and/or alarm systems. The structure shown in FIG. 14 can be made as a three-dimensional multi-level cryo-substrate, in which multiple circuit boards 610 are stacked with a plurality of cryo-storage elements over one another.

The chip-type storage elements can be removed in a frozen state from the circuit board without problems and transferred to other circuit boards, measuring devices, or processing stations, without losing the specimen data. The cryo-storage elements are electronically addressable externally.

In addition, for multiple safeguarding, the cryo-storage elements can be provided with one or more identifiers, automatically readable or visually controllable colored markings. The cryo-storage elements, according to FIG. 15, also allow further miniaturization, compared to the dimensions of common integrated circuits. With miniaturization, an optimal control is preferred, instead of the electrical contact.

The at least one circuit board of a storage substrate can be connected with a computer bus system, with which an individual inquiry and control of the individual cryo-storage elements takes place. The form of the cryo-storage elements shown in FIG. 15 can be modified depending on the application (for example, round or polygonal specimen carriers).

Important features of the invention are condensed in the following description.

The inventive storage substrate combines a material receptacle with a specimen-specific data receptacle. During low-temperature storage, the selective removal of materials (cells, cell suspensions) and the reading/storage of data and/or data material are possible.

The data identification is multiply ensured, in that the specimens and the specimen data storage are arranged on the same or directly adjacent substrate positions. In addition, the storage substrate can be dyed, so that based on the color of the cryo-storage element along and the base body, it can be determined from which storage substrate the respective specimen originates.

The cryo-storage elements can be easily disinfected and reused. Further, they form a protection for the specimens against environmental conditions with the inventive cryo-preservation.

It is also possible to provide the base body and the cryo-storage elements of a storage substrate as one unit with a colored or a digital or analogue identification sample, which allows a clear arrangement of both parts at any time. This has advantages for an automated, optical control (for example, dye and coding detection).

For the first time, specimen data can be stored in ranges of kilobytes to megabytes on the inventive cryo-storage. This is particularly advantageous with the storage of measurement results.

During the expected useful life of a storage substrate, data can be supplemented at any time (data accumulation). In this manner, all data acquired on the specimen or all performed manipulations, measurements, treatments, or the like can be documented specimen-specific completely and without interruption.

Specific treatments of the specimens, in particular, in the chip-type storage elements, can be performed selectively with a procedure programming and storage. For example, in the frame of a cryo-preservation, a predetermined heating, cooling, measuring, controlling, and alarm/display program can operated and be documented in a program data storage. In a frozen state, various temperature or measuring programs can run for different cryo-storage elements. For example, local thawing can be triggered, in order to perform a measurement of the specimen. The above-described heating elements can be used with all embodiments of the inventive storage substrate for a local heating of storage media. On the storage media, localized heating can occur, while the associated specimen remains in a cryo-preserved state.

According to the present invention, it can be provided that the storage substrate is operated combined with a mere electronic data bank, in which the specimen data of the storage substrate are stored in a mirrored fashion.

The covering of the specimen receptacles can be partially or completely transparent. Through this layer, optical and other measuring methods are coupled in the specimen receptacles. For example, the specimens can be shown pictorially. Fluorescent measurements, dielectric measurements, and/or ultrasonic representations are possible.

An inventive cryo-data bank includes a plurality of the above-described storage substrates, a control device, and a processing device for manipulating the storage substrates and for removal of specimens.

The features of the invention disclosed in the foregoing description, the claims, and the drawings can be of importance both individually as well as in desired combinations for the implementation of the invention in its various embodiments.

What is claimed is:

1. A method for storing specimens and specimen data, said method comprising:

arranging a plurality of specimens on a storage substrate; and storing specimen data at specific positions on the storage substrate, wherein the specimen data are characteristic of the respective specimens, and are each uniquely associated with a respective specimen by a respective storage position on the storage substrate, and wherein a respective specimen is arranged on a specimen carrier and associated specimen data are stored in a specimen data storage medium, whereby, respectively, the specimen carrier and the specimen data storage medium form a composite component that is releasable from the storage substrate for specimen removal.

2. The method according to claim 1, wherein the specimen data are stored on, near, or under the associated specimen.

3. The method according to claim 1, wherein the specimen data comprises at least one of: information for identification of the specimens, information about substance features of the specimens, information about measurement results and information about treatment steps.

4. The method according to claim 1, wherein the specimen data are read and/or written in a cooled state of the storage substrate.

5. The method according to claim 1, wherein a specimen is removed from the substrate storage medium in connection with the stored specimen data and is transferred onto another substrate or to a measuring device or a treatment device.

6. The method according to claim 1, wherein the specimen data are stored optically, magnetically, topographically, or electromagnetically.

7. The method according to claim 1, wherein the specimens include suspensions of at least one cell, cell component, cell aggregate, and/or tissue.

8. The method according to claim 7, wherein the specimens include supplementary reference and probe specimens.

9. The method according to claim 1, further comprising measuring at least one frozen, heated or thawed specimen in a cooled state of the remaining storage substrate, and storing measurement results as specimen data.

10. The method according to claim 9, further comprising treating the at least one frozen, heated or thawed specimen.

11. The method according to claim 1, wherein a control of a state of at least one specimen on the storage substrate takes place with a computing circuit associated with the at least one specimen.

12. A storage substrate for cryo-preservation of a plurality of specimens, said storage substrate comprising a plurality of cryo-storage elements, wherein each of the cryo-storage elements respectively comprises a composite component including a specimen carrier and an integrated circuit as a specimen data storage medium.

13. The storage substrate according to claim 12, wherein each of the cryo-storage elements is arranged releasably in a base body of the storage substrate.

14. The storage substrate according to claim 12, wherein each of the cryo-storage elements comprises a molded component including the specimen carrier and the specimen data storage medium.

15. The storage substrate according to claim 12, wherein the at least one specimen carrier is integrated in a structure of the integrated circuit.

16. The storage substrate according to claim 15, wherein the at least one specimen carrier has a cryo-container.

17. The storage substrate according to claim 15, wherein the at least one specimen carrier has at least one hose-shaped, capillary-shaped, or channel-shaped specimen chamber.

18. The storage substrate according to claim 15, wherein the at least one specimen carrier is provided as a channel-shaped specimen receptacle in a substrate of the integrated circuit.

19. The storage substrate according to claim 15, wherein each of the cryo-storage elements contains a computing circuit adapted to manage a function of each of the cryo-storage elements, wherein the computing circuit enables each of the cryo-storage elements to communicate externally.

20. A cryo-storage element comprising a composite of: (a) a specimen carrier for a specimen; and (b) an integrated circuit as a data storage medium for storage of specimen data.

21. A method for operating a cryo-bank, wherein the specimens are cryo-preserved or treated with a method according to claim 1.

* * * * *